(12) United States Patent
Gabizon et al.

(10) Patent No.: US 10,085,940 B2
(45) Date of Patent: Oct. 2, 2018

(54) LIPOSOMES CO-ENCAPSULATING A BISPHOSPHONATE AND AN AMPHIPATHIC AGENT

(75) Inventors: Alberto A. Gabizon, Jerusalem (IL); Yechezkel Barenholz, Jerusalem (IL); Hilary Shmeeda, Givat Zeev (IL); John Maher, London (GB); Ana Catarina Parente Pereira, London (GB)

(73) Assignees: YISSUM RESEARCH DEVELOPMENT COMPANY OF THE HEBREW UNIVERSITY OF JERUSALEM LTD., Jerusalem (IL); KINGS COLLEGE LONDON, London (GB); SHAARE ZEDEK SCIENTIFIC LTD., Jerusalem (IL)

( * ) Notice: Subject to any disclaimer, the term of this patent is extended or adjusted under 35 U.S.C. 154(b) by 1024 days.

(21) Appl. No.: 14/232,332

(22) PCT Filed: Jul. 12, 2012

(86) PCT No.: PCT/IL2012/050249
§ 371 (c)(1),
(2), (4) Date: Jul. 7, 2014

(87) PCT Pub. No.: WO2013/008240
PCT Pub. Date: Jan. 17, 2013

(65) Prior Publication Data
US 2014/0328899 A1 Nov. 6, 2014

Related U.S. Application Data

(60) Provisional application No. 61/507,325, filed on Jul. 13, 2011, provisional application No. 61/507,821, filed on Jul. 14, 2011.

(51) Int. Cl.
| | |
|---|---|
| *A61K 31/704* | (2006.01) |
| *A61K 9/127* | (2006.01) |
| *A61K 31/663* | (2006.01) |
| *A61K 38/20* | (2006.01) |
| *A61K 45/06* | (2006.01) |
| *A61K 35/15* | (2015.01) |
| *A61K 35/17* | (2015.01) |
| *A61K 47/55* | (2017.01) |
| *A61K 47/69* | (2017.01) |
| *A61K 39/00* | (2006.01) |

(52) U.S. Cl.
CPC ............ *A61K 9/127* (2013.01); *A61K 9/1271* (2013.01); *A61K 9/1278* (2013.01); *A61K 31/663* (2013.01); *A61K 31/704* (2013.01); *A61K 35/15* (2013.01); *A61K 35/17* (2013.01); *A61K 38/2013* (2013.01); *A61K 38/2026* (2013.01); *A61K 38/2086* (2013.01); *A61K 45/06* (2013.01); *A61K 47/551* (2017.08);

*A61K 47/6911* (2017.08); *A61K 2039/5158* (2013.01); *A61K 2039/55555* (2013.01)

(58) Field of Classification Search
None
See application file for complete search history.

(56) References Cited

U.S. PATENT DOCUMENTS

| | | |
|---|---|---|
| 4,876,248 A | 10/1989 | Breliere et al. |
| 4,927,814 A | 5/1990 | Gall et al. |
| 5,013,556 A | 5/1991 | Woodle et al. |
| 5,395,619 A | 3/1995 | Zalipsky et al. |
| 5,817,856 A | 10/1998 | Tirosh et al. |
| 6,043,094 A | 3/2000 | Martin et al. |
| 6,165,501 A | 12/2000 | Tirosh et al. |
| 2004/0161457 A1 | 8/2004 | Gabizon |
| 2007/0218116 A1 | 9/2007 | Schwendener |

FOREIGN PATENT DOCUMENTS

| | | |
|---|---|---|
| WO | 9807409 A1 | 2/1998 |
| WO | 2010143193 A1 | 12/2010 |

OTHER PUBLICATIONS

Clyburn et al. Cancer Chemother Pharmacol. 2010, vol. 65, p. 969-978.*
Patrick P. Deluca et al "Parental Drug-Delivery Systems" Pharmaceutics and Pharmacy Practice. 8:236-278 (1982).
Adam Baszkin et al "Physicaly Chemistry of Biological Interfaces" CRC Press 1-849 (1999).
Y. Barenholz et al "Structure and Properties of Membranes" Physical Chemistry of Biologyical171-241 (2000).
Yechezkel Barenholz et al "Liposome application: problems and prospects" Current Opinion in Colloid & Interface Science 6:66-77 (2001).

(Continued)

*Primary Examiner* — Yunsoo Kim
(74) *Attorney, Agent, or Firm* — Browdy and Neimark, PLLC

(57) ABSTRACT

The present disclosure provides liposomes comprising a membrane and an intraliposomal aqueous water phase, the membrane comprising at least one liposome forming lipid and the intraliposomal aqueous water phase comprises a salt of a bisphosphonate together with an amphipathic weak base agent (PLAD). An example of a liposome is one comprising co encapsulated in the intraliposomal aqueous water phase N-containing bisphosphonate, such as alendronate, and an anthracycline such as doxorubicin which was shown to increase survival as compared to Doxil or to administrations of liposomal alendronate (PLA) and Doxil (separate liposomes). Such liposomes may carry a targeting moiety exposed at the liposome's outer surface, for example, conjugate of folic acid as a targeting moiety to folate receptor (FT-PLAD). Also provided by the present disclosure is a method of preparing the liposomes and methods of use of the liposomes, at times, in combination with additional active ingredients, such as γδ T-cells.

12 Claims, 18 Drawing Sheets

(56) References Cited

OTHER PUBLICATIONS

Hilary Shmeeda et al "Delivery of zoledronic and encapsulated in folate-targeted lipsome results in potent in vitro cytotoxic activity on tumor cells" Journal of Controlled Relaease 146:76-83 (Jan. 2010).

Hila Epstein et al "Liposomal Bisphosphonates for the Treatment of Restenosis" Liposome Technology. 3 : 2 : 187-205 (2007).

Dr. Steven W. Dow "Liposomal Bisphosphonate Therapy for Malignant Histiocytosis" Canine health foundation. XP002685497(Jan. 2009).

Karin Fischer et al "The flow cytometric PKH-26 assay for the determination of T-cell mediated cytotoxic activity" Methods 31:135-142 (Apr. 2003).

Alberto Gabizon et al "Targeting Folate Receptor with Folate Linked to Extremities of Poly(ethylene glycol)-Grafted Liposomes: In Vitro Studies" Bioconjugate Chem.10:2: 10:289-298 (Feb. 1999).

Alberto Gabizon et al "In Vivo Fate of Folate-Targeted Polyethylene-Glycol Liposomes in Tumor-Bearing Mice" Clinical Cancer Research 9:6551-6559(Dec. 2003).

PLGA Garbuzenko et al "Electrostatics of PEGylated Micelles and Liposomes Containing Charged and Neutral Lipopolymers" Langmuir 21:2560-2568 (Jan. 2005).

Shigenor Goto et al "The Therapeutic Potential of Immuno-cell Therapy of Cancer in Combination with Aminobisphosphonates" Anticancer Research 26: 3989-3996 (2006).

Jonathan R. Green "Bisphophonates: Preclinical Review" The Oncologist. 9:4:3-13 (2004).

Helen L. Neville-Webbe et al "Potential Anticancer Properties of Bisphosphonates" Elsevier. Seminars in Oncology 37:3:1:S53-S65 (Jun. 2010).

Michele Caraglia et al "Emerging anti-cancer molecular mechanisms of aminobisphosphonates" Endocr Relat Cancer 13:1:7-26 (2006).

Hilary Shmeeda et al "Enzymatic Assays for Quality Control and Pharmacokinetics of Liposome Formulations: Comparison with Nonenzymatic Conventional Methodologies" Methods in Enzymology. 367:17:272-291 (2003).

Oren Tirosh et al "Hydration of Polyethylene Glycol-Grafted Liposomes" Biophysical Journal. 74:1371-1379 (Apr. 1998).

Lawrence A. Trissel "Injectable Drugs" ASHP. 4: 622-630 (Sep. 1986).

Paul S. Uster et al "Insertion of poly(ethylene glycol) derivatized phospholipid into pre-formed liposomes results in prolonged in vivo circulation time" FEBS Letters. 386: 243-246(Feb. 1996).

Scott Wilkie et al "Selective Expansion of Chimeric Antigen Receptor-targeted T-cells with Potent Effector Function using Interleukin-4" Journal of Biological Chemistry. 285:33: 25538-25544 (Aug. 2010).

Gregory Gregoriadis "Quality control assays in the development and clinical use of liposome-based formulations" Liposome Technology 2:1: 527-617 (1993).

Tayar et al "Octan-1-ol-Water Partition Coefficients of Zwitterionic a-Amino Acids. Determination by Centrifugal Partition Chromatography and Factorization into Steric/Hydrophobic and Polar Components" J. Chem Soc. Perkin Trans. 79-84: 2 (1992).

June "Adoptive T cell therapy for cancer in the clinic" The Journal of Clinical Investigation. 117:6:1466-1476 (Jun. 2007).

Amino Acid Structure, Feb. 4, 1997, XP055287598.

* cited by examiner

LIPOSOMES CO-ENCAPSULATING A BISPHOSPHONATE AND AN AMPHIPATHIC AGENT

FIELD OF THE INVENTION

This invention relates to liposomes encapsulating active agents and uses thereof in therapy.

LIST OF REFERENCES

The following list of references is considered to be pertinent for describing the state of the art in the field of the invention.
(1) Green J R Bisphosphonates: Preclinical Review, Oncologist 8 (Suppl 4): 3-13, 2004.
(2) Neville-Webbe H L, Gnant M, Coleman R E. Potential anticancer properties of bisphosphonates. Semin Oncol 37 (Suppl 1):S53-65, 2010.
(3) Caraglia M, Santini D, Marra M, Vincenzi B, Tonini G, Budillon A. Emerging anti-cancer molecular mechanisms of aminobisphosphonates. Endocr Relat Cancer 13(1):7-26, 2006.
(4) Goto S, Noguchi A, Jinguji H, Takahara M. The therapeutic potential of immuno-cell therapy of cancer in combination with aminobisphosphonates. AntiCancer Research 26: 3989-3996 (2006)
(5) US application publication No. 2007/0218116;
(6) Hilary Shmeeda, Yasmine Amitay, Jenny Gorin, Dina Tzemach, Lidia Mak, Joerge Ogorka, Saran Kumar, J. Allen Zhang, Alberto Gabizon in Journal of Controlled Release 146:76-83 (2010);
(7) US application publication No. 2004/0161457.

BACKGROUND OF THE INVENTION

Liposomes have generated a great deal of interest as drug delivery vehicles. In particular, they are constantly being investigated for their ability to improve the delivery of chemotherapeutic agents to tumors, in efforts to increase therapeutic efficacy and decrease toxicity to normal cells. As a result, several liposomal chemotherapeutic agents are now available in the clinic. STEALTH, a liposomal system coated with polyethylene glycol, avoids uptake by the reticuloendothelial system, prolonging liposome circulation time and improving drug delivery to the tumor while generally decreasing toxicity. One FDA approved STEALTH-based drug is the pegylated liposomal doxorubicin sulfate (Doxil/Caelyx).

A group of drugs which has recently attracted considerable interest in cancer medicine is the bisphosphonates. Bisphosphonates are used primarily to increase bone density and reduce the risk of fracture in patients with osteoporosis, to slow bone turnover in patients with Paget's disease of the bone, and to treat bone metastases and normalize elevated levels of blood calcium in patients with cancer [Green J. R. Biophosphonates: preclinical review, Oncologist 8 (suppl 4) 3-13, 2004]. Zoledronic acid and other N-containing bisphosphonates have also been found to interfere with critical processes in cell signaling and growth at nanomolar concentrations and are currently under evaluation for use in combination therapies for various anti-tumor applications irrespective of bone metastases [Neville-Webbe H L, Gnant M, Coleman R E. Potential anticancer properties of bisphosphonates. Semin Oncol 37 (Suppl 1):553-65, 2010.]. In addition to direct anti-tumor effect, anti-angiogenic effects [Caraglia M, Santini D, Marra M, Vincenzi B, Tonini G, Budillon A. Emerging anti-cancer molecular mechanisms of aminobisphosphonates. Endocr Relat Cancer 13(1):7-26, 2006] and immunological effects that can mediate indirect antitumor effects have also been demonstrated [Goto S, Noguchi A, Jinguji H, Takahara M. The therapeutic potential of immuno-cell therapy of cancer in combination with aminobisphosphonates. AntiCancer Research 26: 3989-3996, 2006].

However, bisphosphonates are rapidly cleared from plasma by the kidneys and, apart from bone, have very low cellular permeability and minimal tissue penetration and this substantially limits their anti tumor efficacy.

Bisphosphonate-liposomes formulations have been described, for example, in US application publication No. 2007/0218116 which describes a method for treating or preventing tumor growth and metastasis by administrating liposomal bisphosphonates. In addition, delivery of zoledronic acid encapsulated in folate-targeted liposome which resulted in potent in vitro cytotoxic activity on tumor cells was also described [Hilary Shmeeda, Yasmine Amitay, Jenny Gorin, Dina Tzemach, Lidia Mak, Joerge Ogorka, Saran Kumar, J. Allen Zhang, Alberto Gabizon in Journal of Controlled Release 146 (2010) 76-83].

US application publication No. 2004/0161457 describes a method for administrating a therapeutic compound encapsulated in liposome to multi-drug resistant cancer cells. This method also included a covalently attached folate ligand to the liposome carrier.

SUMMARY OF THE INVENTION

In accordance with a first of its aspects, the present disclosure provides liposomes comprising a membrane and an intraliposomal aqueous water phase, the membrane comprising at least one liposome forming lipid and the intraliposomal aqueous water phase comprises a salt of a bisphosphonate and an amphipathic weak base agent.

In accordance with a second aspect, the present disclosure provides a method for co-encapsulating in a same liposome a bisphosphonate and an amphipathic weak base agent, the method comprising:
  providing a suspension of liposomes comprising a membrane and an intraliposomal water phase, the membrane the membrane comprising at least one liposome forming lipid and the intraliposomal water phase comprising encapsulated therein, a bisphosphonate;
  incubating the liposomes encapsulating the bisphosphonate with an amount of an amphipathic weak base agent to allow co-encapsulation of the bisphosphonate and the amphipathic weak base agent whereby a salt between the bisphosphonate and the amphipathic weak base agent is formed.

In accordance with yet a third of its aspects, the present disclosure provides the liposomes for use in the treatment of a pathological condition, e.g. proliferative disease or disorder.

In accordance with a fifth of its further aspects, the present disclosure provides the use of the liposomes as defined, for the preparation of a pharmaceutical composition.

In accordance with a further aspect, the present disclosure provides a method of treatment comprising administering to a subject an amount of liposomes as defined, in combination with an amount of immune cells such as $\gamma\delta$ T-cells, the combination providing a therapeutic effect that is greater than the effect obtained with treatment with only the liposomes encapsulating the salt comprising said bisphosphonate and amphipathic weak base.

Finally, the present disclosure provides a package comprising a first composition comprising liposomes as defined and a second composition comprising immune cells, such as γδ T-cells, and instructions for the combined use of the first and second composition for treatment of a subject, the combined use providing a therapeutic effect that is greater than the effect obtained with only said liposomes.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3A shows equal low cell uptake by KB human head-and-neck carcinoma cells of DOX when Doxil and L-ALD/DOX are compared; FIGS. 3B-3D show, respectively, in vitro cytotoxicity of L-ALD/DOX compared to that of Doxil in KB cells, N87 human gastric carcinoma cells and IGROV human ovarian carcinoma cells.

FIGS. 4B and 4C show a comparison of plasma levels of doxorubicin 24 h after i.v injection with either a commercial liposomal doxorubicin (Doxil) or the co-encapsulating L-ALD/DOX ("L-BP-DOX"); the bars show that the plasma levels of doxorubicin are similar for L-ALD/DOX("L-BP-DOX") and for Doxil, thus indicating that the L-ALD/DOX ("L-BP-DOX") is at least as long-circulating (20% of the injected dose at 24 h) and stable in vivo as the commercially available alternative Doxil.

FIG. 5A is a graph demonstrating increased anti-tumor activity of L-ALD/DOX in M109R tumor compared to Doxil; FIGS. 5B-5D are graphs showing the individual tumor growth curves in the M109R model, from which FIG. 5A is formed, with FIG. 5B showing individual curves for untreated mice, FIG. 5C showing the curves for Doxil treated mice and FIG. 5D showing the curves for L-ALD/DOX treated mice.

DETAILED DESCRIPTION OF EMBODIMENTS

Figure 1A:
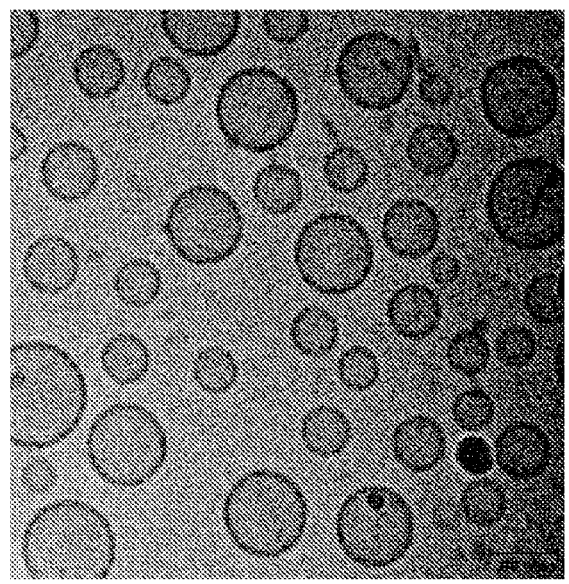
FIGS. 1A-1B are cryo-transmission electron microscopy (Cryo-TEM) images before (FIG. 1A) and after (FIG. 1B) foxorubicin loading (L-ALD/DOX formulation also referred to as pegylated liposomal alendronate of doxorubicin, PLAD) showing in FIG. 2B spherical vesicles with precipitated salt of doxorubicin-alendronate (rod-like formations) in the interior water phase.
Figure 1B:
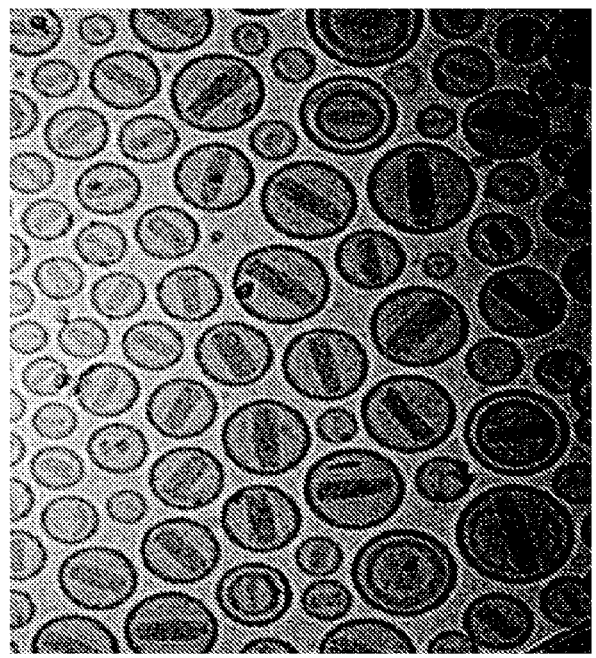

The present disclosure is based on the new finding that it is possible co-encapsulate in the same liposome two active drugs (i) a bisphosphonate which is anionic and negatively charged over a broad pH range (probably due to the low pKa of its phosphates and therefore membrane impermeable) and (ii) an amphipathic weak base (AWB) agent; the loading of the two active drugs form a salt there between with a high mole:mole ratio of each drug with respect to lipid(s) forming the liposomes.

The present disclosure is also based on the finding that the driving force for loading of the AWB agent is a transmembrane ammonium bisphosphonate gradient obtained by passive encapsulation of ammonium bisphosphonate. Without being bound by theory, it is assumed that upon AWB loading, the bisphosphonate anion acts as the counter ion to the AWB, which leads to organization of the AWB agent in the intraliposome aqueous phase in a manner different from that obtained in the presence of sulfate as the counter ion (when using ammonium sulfate). In addition, the sulfate is basically an excipient and not an active agent.

The present disclosure is further based on the finding that co-encapsulated bisphosphonate and AWB agent form together a salt that allow the high and chemically and physically stable (e.g. no significant leakage) retention of the two agents in the liposome.

Further, the invention is based on the finding that due to the manner of loading the two active drugs where the bisphosphonate is loaded in a salt form (e.g. ammonium bisphosphonate, and not in the acid or free form) and the AWB is added in an amount lower than the molar quantity of bisphoshonate (alendronate), residual amount of ammonium bisphosphonate may be present in the intraliposomal water phase after loading of the AWB agent. In addition, for the same reason, namely, the use of excess amount of the bisphosphonate as compared to the AWB agent, in the intraliposomal water phase of the final liposome, residual amount of bisphosphonate, not in a salt form with the AWB agent, is present in the liposome water phase. These residual amounts of substances may be used as markers indicative that the liposomes were formed in accordance with the method of the present invention. In this connection it is noted that while bisphosphonate in its free from may also act as a driving force for the loading of the AWB agent, the loading was found to be less efficient and less stable than the result obtained when loading with a salt form of the bisphosphonate (ammonium bisphosphonate salt).

Thus, in accordance with the first aspect of the present disclosure, there are provided liposomes comprising a membrane and an intraliposomal aqueous water phase, the membrane comprising at least one liposome forming lipid and the intraliposomal aqueous water phase comprising a salt of a bisphosphonate and an amphipathic weak base (AWB) agent.

The liposomes in the context of the present disclosure are any organized collection of lipids forming at least one type of liposomes, and enclosing at least one intraliposomal aqueous compartment. The liposomes may be unilamellar, bilamellar or even, at times, multilamellar. Various types of liposomes may be used in accordance with the invention, from small unilamellar vesicles (SUV), large unilamellar vesicles (LUV), multilamellar vesicles (MLV), multivesicular vesicles (MVV), large multivesicular vesicles (LMVV, also referred to, at times, by the term giant multivesicular vesicles, "GMV"), oligolamellar vesicles (OLV), and others.

When the liposomes are unilamellar vesicles, the AWB agent and the bisphosphonate are typically enclosed within the internal aqueous water phase of the liposome; when the liposome is bi or multilamellar vesicle, the AWB agent and the bisphosphonate may be enclosed within the internal water phase but also in the aqueous phases between the vesicle's lamellae.

In one particular embodiment, the liposomes are unilamellar liposomes.

In one embodiment, the liposomes have a mean diameter in the range of 50 to 150 nm.

The liposomes comprise at least one liposome forming lipid. The "liposome forming lipids" are primarily selected from glycerophospholipids and sphingomyelins which when dispersed in aqueous media, at a temperature above their solid ordered to liquid disordered phase transition temperature, self-form stable liposomes.

The glycerophospholipids have a glycerol backbone wherein at least one, preferably two, of the hydroxyl groups is substituted by one or two of an acyl, alkyl or alkenyl chain, and the third hydroxyl group is substituted by a phosphate (phosphatidic acid) or a phospho-ester such as phosphocholine group (as exemplified in phosphatidylcholine), being the polar head group of the glycerophospholipid or combination of any of the above, and/or derivatives of same and may contain a chemically reactive group (such as an amine, acid, ester, aldehyde or alcohol). The sphingomyelins comprise, as an example, N-palmitoyl sphingomyelin, N-stearoyl sphingomyelin and other ceramides (N-acyl sphingosines) varied in their acyl chains unit having a phosphocholine moiety attached to ceramide position 1 as the polar head group. The amide of ceramides can be replaced by other types of bonds such as a C—C bond as is the case for ceramines Typically, the substituting chain, e.g. the acyl, alkyl or alkenyl chain in the glycerophospholipids or sphingolipid, is between about 14 to about 24 carbon atoms in length, and has varying degrees of saturation, thus resulting in fully, partially or non-hydrogenated (liposome-forming) lipids.

Te lipids may be of a natural source, semi-synthetic or a fully synthetic lipid, and may be neutral, negatively or positively charged. There are a variety of synthetic vesicle-forming lipids and naturally-occurring vesicle-forming lipids.

In one preferred embodiment, the lipid is a phospholipid and more specifically, a phosphatidylcholine (PC) based phospholipid (lipid having a phosphocholine headgroup), including, without being limited thereto, substituted PC, hydrogenated soy phosphatidylcholine (HSPC), Dipalmitoylphosphatidylcholine (DPPC), egg yolk phosphatidylcholine (EPC), 1-palmitoyl-2-oleoylphosphatidyl choline (POPC), distearoylphosphatidylcholine (DSPC), dimyristoyl phosphatidylcholine (DMPC).

As to the sphingolipid, these may include, without being limited thereto, sphingomyelin, N-palmitoyl sphingomyelin, N-stearyl sphingomyelin, ceramide.

Lipids having a relatively high $T_m$ (above physiological body temperature) may be referred to as "rigid" lipids, typically those having saturated, long acyl chains, while lipids with a relatively low $T_m$ (below physiological body temperature) may be referred to as "fluid" lipids. Fluidity or rigidity of the liposome may be determined by selecting lipids with pre-determined fluidity/rigidity for use as the liposome-forming lipids. In accordance with one embodiment, the $T_m$ of the lipid(s) forming the liposomes are preferably selected such that their $T_m$ or the $T_m$ of their combination is equal to or above 40° C. Some phosphatidylcholine based lipids have a $T_m$ above 40° C. and typically have two acyl or alkyl chains with 16 or more carbon atoms. These include, without being limited thereto, hydrogenated soy PC (HSPC) having a Tm of 53° C., Dipalmitoylphosphatidylcholine (DPPC), having a $T_m$ of 41.3° C., N-palmitoyl sphingomyelin having a $T_m$ of 41.2° C., distearylphosphatidylcholine (DSPC) having a $T_m$ of 55° C., N-stearoyl sphingomyelin having a $T_m$ of 48° C., All these $T_m$ temperature data are available from http://www.avantilipids.com providing Phase Transition Temperatures or from http://www.lipidat.chemistry.ohio-state.edu, both sites being well known to those versed in the art. [see also Barenholz, Y., Liposome application: problems and prospects. Curr. Opin. Colloid Interface Sci. 6, 66-77 (2001); Barenholz, Y. and Cevc, G., Structure and properties of membranes. In Physical Chemistry of Biological Surfaces (Baszkin, A. and Norde, W., eds.), Marcel Dekker, NY (2000) pp. 171-241].

As to the active components enclosed within the liposomes, these include one or more bisphosphonate and one or more AWB agent.

With respect to the bisphosphonate, these include preferably N-containing bisphosphonates.

N-containing bisphosphonate are those having a $PX_3$—$CR_1R_2$—$PX_3$ backbone, where X is either H or —OH. The N-containing bisphosphonate are those carrying N-containing substituents at $R_1$ and/or $R_2$, such as those presented in the following Table 1:

TABLE 1

N-containing bisphosphonates

| Common name | $R_1$ | $R_2$ |
|---|---|---|
| Alendronate | —OH | —$(CH_2)_3$—$NH_3$ |
| Pamidronate | —OH | —$(CH_2)_2$—$NH_3$ |
| neridronate | —OH | —$(CH_2)_5$—$NH_3$ |
| Olpadronate | —OH | —$(CH_2)_2N(CH_3)_2$ |
| Ibandronate | —OH | —$(CH_2)_2N(CH_3)(CH_2)_4CH_3$ |
| Risedronate | —OH | (3-pyridinylmethyl group) |
| Zoledronate | —OH | (imidazol-1-ylmethyl group) |

The above N-containing bisphosphonates are also known by the following nomenclature:

Alendronate—alendronic acid, 4-amino-1-hydroxybutylidene-1,1-bisphosphonic acid, alendronate sodium or monosodium trihydrate; described in U.S. Pat. No. 4,922,007 and U.S. Pat. No. 5,019,651, both of which are incorporated by reference herein in their entirety);

Ibandronate—1-hydroxy-3-(N-methyl-N-pentylamino) propylidene-1,1-bisphosphonic acid, also known as BM-210955, described in U.S. Pat. No. 4,927,814, which is incorporated by reference herein in its entirety;

Neridronate—6-amino-1-hydroxyhexylidene-1,1-bisphosphonic acid;

Olpadronate—3-(dimethylamino)-1-hydroxypropylidene-1,1-bisphosphonic acid;

Pamidronate—3-amino-1-hydroxypropylidene-1,1-bisphosphonic acid;

Risedronate—1-hydroxy-2-(3-pyridinyl)-ethylidene-1,1-bisphosphonic acid;

Zoledronate—zoledronic acid, 1-hydroxy-2-(1H-imidazol-1-yl)ethylidene-1,1-bisphosphonic acid.

Other N-containing bisphosphonates are [2-(2-pyridinyl) ethylidene]-1,1-bisphosphonic acid (piridronate, described in U.S. Pat. No. 4,761,406, which is incorporated by reference in its entirety); 4-chlorophenyl)thiomethane-1,1-disphosphonic acid (tiludronate, described in U.S. Pat. No. 4,876,248, which is incorporated herein by reference in its entirety).

The N-containing bisphosphonate also include pharmaceutically acceptable salts and derivatives thereof. As used herein, the terms "pharmaceutically acceptable" which may be used interchangeably with the term "physiologically acceptable" refer to substances that are "generally regarded as safe" (GRAS), e.g., that are physiologically tolerable and typically do not produce an allergic or similar untoward reaction, such as gastric upset, dizziness and the like, when administered to an animal. Preferably, "pharmaceutically acceptable" or "physiologically acceptable" mean approved by a regulatory agency of the Federal or a state government or listed in the U.S. Pharmacopeia or other generally recognized pharmacopeia for use in animals.

Non-limiting examples of pharmaceutically acceptable salts include those selected from the group consisting alkali metal, alkaline metal, ammonium, and mono-, di, tri-, or tetra-Q-Cso-alkyl-substituted ammonium. Some particular salts are those selected from the group consisting of sodium, potassium, calcium, magnesium, and ammonium salts. Non-limiting examples of derivatives include those selected from the group consisting of esters, hydrates, and amides.

With respect to the amphipathic weak base (AWB) agents, the term "weak base" is to be understood as having the common chemical meaning of a weak base, i.e. a chemical base that does not ionize fully in a pure aqueous medium. Specifically, a weak base can be defined as any substance having a pKa equal or below 11 and a log D at pH 7 in the range between −2.5 and 1.5.

AWB agent may be selected from the group of compounds including, without being limited thereto, anthracyclines (e.g. doxorubicin, epirubicin, daunorubicin, idarubicin, amrubicin) anthraquinones (e.g. mitoxantrone), vinca alkaloids (e.g. vincristine, vinblastine, vinorelbine), and camptothecin derivatives (e.g. topotecan, irinotecan, SN-38 (7-ethyl-10-hydroxycamptothecin)).

In one embodiment, the AWB agent is a cytotoxic agent. An amphipathic weak base agent of particular interest in accordance with the disclosure is doxorubicin (DOX).

In some embodiments, the combination of bisphosphonate and AWB agent is such that for a pathological condition (disease, disorder etc), the bisphosphonate, in its conventional, free form, of administration, is regarded by practitioners, according to conventional standards and statistics, therapeutically ineffective, at least in cancer. However, a liposome encapsulating the bisphosphonate and an AWB agent (known to be given for the selected condition) has a therapeutic effect against the selected condition that is greater than the effect of the AWB agent encapsulated in the same liposome, albeit, without said bisphosphonate (encapsulated alone). At times, the liposomes encapsulating the bisphosphonate and an AWB agent (known to be given/effective for the selected condition) has a therapeutic effect against the selected condition in statistically significant lower doses of the AWB agent when given alone (in liposomes, albeit without the bisphosphonate). In other words, the co-encapsulated bisphosphonate may be regarded as augmenting the response to the AWB agent.

The bisphosphonate and the AWB agent act as counter ions to each other, forming together, within the intraliposomal aqueous water phase, a salt. This salt precipitates within the intraliposomal aqueous water phase once the solubility limits are exceeded during the co-encapsulation process.

In accordance with some embodiments, the liposomes further comprise membrane active sterols (e.g. cholesterol) and/or phosphatidylethanolamines that may be effective to decrease the membrane's free volume and thereby permeability and leakage of material loaded therein.

In one embodiment, the membrane comprises cholesterol. The amount of the cholesterol is preferably such that the phospholipid/cholesterol mole:mole ratio in the liposome membrane is in the range of between about 75:25 and about 50:50.

In yet some other embodiments, the liposomes also include a lipid derivatized with a hydrophilic polymer to form new entities known by the term lipopolymers. Lipopolymers preferably comprise lipids (liposome forming lipids as well as lipids that do not from into lipids, such as phosphatidylethanolamines) modified at their head group with a polymer having a molecular weight equal to or above 750 Da. The head group may be polar or apolar; however, it is preferably a polar head group to which a large (>750 Da), highly hydrated, flexible polymer is attached. The attachment of the hydrophilic polymer head group to the lipid region may be a covalent or non-covalent attachment; however, it is preferably via the formation of a covalent bond (optionally via a linker). The outermost surface coating of hydrophilic polymer chains is effective to provide a liposome with a long blood circulation lifetime in vivo.

Examples have been described in Tirosh et al. [Tirosh et al., Biopys. J., 74(3):1371-1379, (1998)] and in U.S. Pat. Nos. 5,013,556; 5,395,619; 5,817,856; 6,043,094; and 6,165,501; incorporated herein by reference; and in WO 98/07409. The lipopolymers may be non-ionic lipopolymers (also referred to at times as neutral lipopolymers or uncharged lipopolymers) or lipopolymers having a net negative or a net positive charge.

There are numerous polymers that may be attached to lipids. Polymers typically used as lipid modifiers include, without being limited thereto: polyethylene glycol (PEG), polysialic acid, polylactic acid (also termed polylactide), polyglycolic acid (also termed polyglycolide), polylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers.

The lipopolymer may be introduced into the liposome in two different ways either by: (a) adding the lipopolymer to a lipid mixture, thereby forming the liposome, where the lipopolymer will be incorporated and exposed at the inner and outer leaflets of the liposome bilayer [Uster P. S. et al. FEBBS Letters 386:243 (1996)]; or (b) first preparing the liposome and then incorporating the lipopolymers into the external leaflet of the pre-formed liposome either by incubation at a temperature of ≥40° C., or above the average $T_m$ of the lipopolymer and liposome-forming lipids, or by short-term exposure to microwave irradiation.

While the lipids derivatized into lipopolymers may be neutral, negatively charged, or positively charged, i.e. there is no restriction regarding a specific (or no) charge, the most commonly used and commercially available lipids derivatized into lipopolymers are those based on phosphatidyl ethanolamine (PE), usually, distearylphosphatidylethanolamine (DSPE).

A specific family of lipopolymers which may be employed by the invention include monomethylated PEG attached to DSPE (with different lengths of PEG chains, the methylated PEG referred to herein by the abbreviation PEG) in which the PEG polymer is linked to the lipid via a carbamate linkage resulting in a negatively charged lipopolymer. Other lipopolymer are the neutral methyl polyethyleneglycol distearoylglycerol (mPEG-DSG) and the neutral methyl polyethyleneglycol oxycarbonyl-3-amino-1,2-propanediol distearoylester (mPEG-DS) [Garbuzenko O. et al., Langmuir. 21:2560-2568 (2005)]. The PEG moiety preferably has a molecular weight of the PEG head group is from about 750 Da to about 20,000 Da. More preferably, the molecular weight is from about 750 Da to about 12,000 Da, and it is most preferably between about 1,000 Da to about 5,000 Da. One specific PEG-DSPE employed herein is a PEG moiety with a molecular weight of 2000 Da, designated herein 2000PEG-DSPE or 2kPEG-DSPE.

Liposomes including such derivatized lipids typically include between 1-20 mole percent of such a derivatized lipid in the liposome formulation.

The liposome may include other constituents. For example, charge-inducing lipids, such as phosphatidylglycerol, may also be incorporated into the liposome bilayer to decrease vesicle aggregation, and to increase interaction with cells. Buffers at a pH suitable to make the liposome surface's pH between 6 to 7 can decrease phospholipid hydrolysis. Addition of an antioxidant, such as vitamin E, or chelating agents, such as deferoxamine or DTPA, may be used.

The co-encapsulating liposome may also comprise targeting moiety exposed at the liposome's outer surface. The targeting moiety may be any ligand that can associate with the outer surface of the liposome and have affinity to target tissue or target organ. Some non-limiting targeting moieties include folic acid, Luteinizing-hormone-releasing hormone (LH-RH); the growth inhibiting hormone, somatostatin, the blood plasma protein, transferrin; target specific antibodies such as anti-Her2, anti-EGFr, anti-nucleosome, anti-CD20, anti-transferrin receptor, and anti-folate receptor. A particular embodiment of the present disclosure concerns folate-targeted liposomes. These ligands are generally attached to the liposome membrane by coupling them to a liposome membrane-compatible lipid anchor with or without a spacer molecule. In the present disclosure, as one non-limiting example, the lipid anchor incorporating into the liposome membrane is distearoyl-phosphatidyl-ethanolamine, which is attached, via the spacer molecule of polyethylene-glycol ranging between 1 to 5K molecular weight, to the targeting ligand, folic acid.

In some embodiment, the targeting moiety is linked to the same lipopolymer, but longer than the lipopolymer used in the absence of a targeting moiety. A particular embodiment consists of a liposome containing folate-derivatized $^{3350}$PEG-DSPE, and mPEG$^{2000}$-DSPE, at respective molar ratios of 0.5% and 5% of total liposomal lipid.

In a further aspect, the present disclosure provides a method for co-encapsulating in a same liposome a bisphosphonate and an amphipathic weak base agent, the liposomes being as defined above. The method comprises:

providing liposomes comprising a membrane and an intraliposomal water phase, the membrane comprising at least one liposome forming lipid and the intraliposomal water phase comprising encapsulated therein, a bisphosphonate in a free or salt form (referred to herein, at times, as the initial salt form, namely, before forming a salt with the AWB agent);

incubating the liposomes encapsulating the bisphosphonate with an amount of an amphipathic weak base agent to allow co-encapsulation of the bisphosphonate and the amphipathic weak base agent whereby a final salt between the bisphosphonate and the amphipathic weak base agent is formed.

As noted, prior to incubation with the AWB agent, the bisphosphonate may be present in the liposome in a free form, such as alendronic acid, or in a salt form such as ammonium alendronate. According to some preferred embodiments, the bisphosphonate is in a salt form.

In accordance with some embodiments, the liposomes encapsulating at least one bisphosphonate are in the form of a suspension. The suspension of liposomes may be prepared in various techniques. In one embodiment, the suspension of liposomes is formed by rehydrating a dry mixture of components for forming the liposome, such as the liposome forming lipids, the sterols etc. with a buffer containing the bisphosphonate. The dry mixture of the constituents used to form the liposome, may be lyophilized and rehydrated when in the form of a dry cake. The rehydration would typically be at a temperature above the $T_m$ of the liposome forming lipids. The rehydration process typically achieves passive encapsulation of the bisphosphonate in the intra-liposomal water phase formed from the liposome forming lipids, which is followed by downsizing the thus formed liposomes to the desired dimensions.

Downsizing may be achieved, for example, by extrusion through polycarbonate membranes using an extruder with a pre-selected pore size (typically the pore size ranges from 1000 nm to 50 nm). The final particle sizes are typically 50-200 nm as measured, and at times 50 nm o 150 nm, depending, inter alia, on the pore size used. The non-encapsulated bisphosphonate is then removed by dialysis, diafiltration, chromatography, and/or use of an anion-exchange bisphosphonate-binding resin (e.g. Dowex anion exchange resin).

The bisphosphonate is passively encapsulated in liposomes during the lipid hydration step the form of a salt with ammonium (aminobisphosphonate). After the liposomes are brought to the desired size, non-encapsulated bisphosphonate is removed by any acceptable method. This is regarded as the initial bisphosphonate salt. The AWB agent is then added to a suspension of the bisphosphonate-containing liposomes by incubating the liposomes with the AWB agent dissolved in a small amount of a physiologic saline.

In accordance with some embodiments, the incubation of the bisphosphonate containing liposomes with the AWB agent is at a temperature that is above the liposome forming lipids' $T_m$. Without being bound by theory it is believed that the heating of the liposomes to a temperature above the liposome's lipids $T_m$, fluidizes the liposomes and thus increases its permeability to the AWB agent.

Further, without being bound by theory, it is believed that the bisphosphonates already present within the liposomes act as the driving force for remote loading the AWB agent with a proton gradient across the liposomes' membrane.

It has been found that by the method disclosed herein it is possible to obtain relatively high amounts of bisphosphonates and AWB agent co-encapsulated in stable form within the liposomes. Without being bound by theory, it is stipulated that the stability is formed, inter alia, due to the formation of a salt between the bisphosphonate and AWB agent.

In accordance with one embodiment, when the $T_m$ of the lipids forming the liposome is less than 60° C., the liposomal bisphosphonates may be heated to a temperature of 60° C. for a time sufficient to allow loading of the amphipathic drug (e.g. 0.5-2 hours) and immediately after loading has completed the liposomes are immediately cooled to a temperature below the liposome's $T_m$. The time required to sufficiently load the amphipathic drug may be determined empirically as these process are typically very fast and reach a plateau of maximal encapsulation within less than an hour.

The resulting liposomes may be considered chemically and physically stable under storage conditions (e.g. 4° C., in biological fluids) for at least several months.

Physical stability of the liposomes may be examined by one or more of the following parameters:
a) assembly size distribution by dynamic light-scattering (DLS).
b) level of free drug by chromatography or spectroscopy which is based on determining of the drugs/phopspholipid mole ratio in a pellet and in the supernatant.

Chemical stability of liposomes may be examined by one or more of the following parameters:
a) measurement of dispersion pH (pH meter)
b) phospholipid acylester hydrolysis by determination of change in non-esterified (free) fatty acids (NEFA) released upon PL hydrolysis [Barenholz et. al. From Liposomes: a practical approach, 2nd Edn., RRC New ed, IRL Press Oxford, 1997] or by TLC [Y. Barenholz, and S. Amselem., (1993) Supra].

In some embodiments, the amount of the AWB agent introduced into the rehydrated bisphosphonates is such that the mole ratio between the AWB agent and the bisphosphonate is between 0.1 and 2, and at times between 0.5 to 1.

In accordance with the present disclosure, the co-encapsulating liposomes may be used for the treatment of a pathological condition. In some embodiments, the pathological condition is a proliferative disease or disorder.

In some embodiments, the proliferative disease or disorder is cancer.

The cancer may be a type for which at least the AWB agent is known to be effective. In one embodiment, the amphipathic weak base agent is doxorubicin and the proliferative disease may be any one of breast cancer, ovarian cancer, multiple myeloma, leukemias, lymphomas, lung cancer, gastric cancer, bladder cancer, prostate cancer, bone sarcomas, and soft tissue sarcomas. Yet further, the use may be for any pathological conditions for which the combination of the bisphosphonate and the amphipathic drug are found to be effective.

Further provided by the present disclosure is a pharmaceutical composition comprising as active ingredient the co-encapsulating liposomes defined herein in combination with a physiologically acceptable carrier.

Yet further provided by the present disclosure is a method for treating a pathological condition, e.g. a proliferative disease or disorder comprising administering to a subject in need an amount of the co-encapsulating liposomes as defined herein.

The term "administering" (or "administration") is used to denote the contacting or dispensing, delivering or applying of the co-encapsulating liposomes to a subject by any suitable route of delivery thereof to the desired location in the subject, including parenteral (including subcutaneous, intramuscular and intravenous, intra-arterial, intraperitoneal, etc.) and intranasal administration, as well as intrathecal and infusion techniques.

According to one embodiment, the co-encapsulating liposomes are formulated in a form suitable for injection. The requirements for effective pharmaceutical vehicles for injectable formulations are well known to those of ordinary skill in the art [See Pharmaceutics and Pharmacy Practice, J.B. Lippincott Co., Philadelphia, Pa., Banker and Chalmers, eds., pages 238-250 (1982), and ASHP Handbook on Injectable Drugs, Toissel, 4th ed., pages 622-630 (1986)].

Further, the present disclosure provides a method of treating a subject for a disease or disorder, the method comprising administering to said subject an amount of liposomes prepared by the method of the invention.

As used herein the term "treatment" (or "treating") denotes curing of an undesired pathological condition or prevention of a condition from developing. For the purpose of curing, the term "treatment" includes direct effect on the causative of the diseases, such as reducing tumor load, preventing cancer related cells from proliferating, etc, as well as indirect effect, e.g. for ameliorating undesired symptoms associated with the disease, slowing down progression of the condition, delaying the onset of a progressive stage of the condition, slowing down deterioration of such symptoms, enhancing onset of a remission period of the condition, if existing, delaying onset of a progressive stage, improving survival rate or more rapid recovery from the condition, lessening the severity of or curing the condition, etc. Treatment also includes prevention of a disease or disorder. The term "prevention" includes, without being limited thereto, administering an amount of the composition to prevent the condition from developing or to prevent irreversible damage caused by the condition, to prevent the manifestation of symptoms associated with the condition before they occur, to inhibit the progression of the condition etc.

The pharmaceutical composition may be provided as a single dose, or in several doses to be administered more than once, for an extended period of time (e.g. to produce cumulative effective amount) in a single daily dose for several days, in several doses a day, etc.

The treatment regimen and the specific formulation of the pharmaceutical composition to be administered will depend on the type of disease to be treated and may be determined by various considerations, known to those skilled in the art of medicine, e. g. physicians. The term "amount effective for" or similar is used herein to denote the amount of the combination of the bisphosphonate and the AWB agent, which, when loaded into the liposome, is sufficient in a given therapeutic regimen to achieve a desired therapeutic effect with respect to the treated disease or disorder. The amount is determined by such considerations as may be known in the art and depends on the type and severity of the condition to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors, including the mode of administration, type of liposome carrying the N-containing bisphosphonate and the amphipathic weak base drug, the reactivity of each of the bisphosphonate and the AWB agent, the liposome's distribution profile within the body, a variety of pharmacological parameters such as half-life in the body after being released from the liposome, undesired side effects, if any, factors such as age and gender of the treated subject, etc.

The present disclosure also provides a combination therapy, namely, a method where the two liposomes are combined with at least one other active substance. Accordingly, there is provided herein a method of treatment comprising administering to a subject an amount of liposomes as defined herein, in combination with an amount of immune cells.

In the context of this aspect of the present disclosure, the immune cells are any cells or part of cells that participate in the immune system cascade. These may include, without being limited thereto, leukocytes, lymphocytes, natural killer (NK) cells, macrophages, monocytes, antigen-presenting cells, dendritic cells, basophils, mast cells.

In some embodiments, the immune cells are lymphocytes. Lymphocytes include B cells and T cells.

In some other embodiments, the immune cells are T cells. In one embodiment, the T cells are γδ T-cells. The γδ T-cells are a small subset of T cells that possess a distinct T cell receptor (TCR) on their surface. Specifically, the γδ T-cells are made up of one γ-chain glycoprotein and one δ-chain glycoprotein, as opposed to the majority of T cells having a TCR composed of two glycoprotein chains called α- and β-TCR chains.

As surprisingly found and shown herein, when treatment comprises a combination of the liposomal L-ALD/DOX (also referred to herein as pegylated liposomal alendronate and doxorubicin, or PLAD) according to the present disclosure and a population of γδ T-cells the effect of the liposomal treatment was augmented. The effect was even more pronounced when folate targeted liposomes were used.

In some embodiments, the combination therapy disclosed herein provides a therapeutic effect that is greater than the effect obtained with treatment with only said liposomes. In some embodiments, the effect provided is such that the amount of liposome administered may be significantly reduced according to acceptable statistical tests and still obtain a therapeutic effect.

In some embodiments, the immune cells are administered to the subject by infusion. The infusion may be of any acceptable type. In some embodiments, the infusion is intravenous (i.v.) infusion or intraperitoneal (i.p.) infusion.

The immune cells may administered to the subject, before, concomitant or after administration of the liposomes. However, in some preferred embodiments, the immune cells are administered after administration of the liposomes. In some embodiments, administration may be several hours after administration of the liposomes and at times at least a day after administration of the liposomes or within a time window of 1-3 days after administration of the liposomes. In this context, when referring to several hours it is to be understood as meaning, at least 3 hours, at times up to 24 hours after treatment with the liposomes. Without being bound by theory it is believed that the time interval between administrations allows sufficient time for the target cells (e.g. tumor cells) to be first sensitized by the liposomes and only thereafter be treated by the immune cells.

The immune cells may be administered together with an immunotimulating agent, such as a cytokine. In some embodiments, the cytokine may be any one selected from the group consisting of interleukins (for example, IL-2, IL-4, IL-15).

As shown in the non-limiting examples provided herein, the combined treatment of the liposomes and the immune cells provide a therapeutic effect that is greater than the effect obtained with treatment with only said liposomes.

The combined treatment is particularly suitable for the treatment of a proliferative disease or disorder, such as, without being limited thereto, cancer.

Also provided herein is a package and method of treatment using the package comprising a first composition comprising liposomes as defined herein and a second composition comprising immune cells; the package also comprises instructions for the combined use of the first and second composition for treatment of a subject. In some preferred embodiments, the combined use provides a therapeutic effect that is greater than the effect obtained with treatment of the same condition with only said liposomes.

It is noted that the forms "a", "an" and "the" as used in the specification include singular as well as plural references unless the context clearly dictates otherwise. For example, the term "a lipid" includes one or more, of the same or different lipids.

Similarly, reference to the plural includes the singular, unless the context clearly dictates otherwise.

Further, as used herein, the term "comprising" is intended to mean that the liposome includes the recited constituents, but does not exclude others which may be optional in the formation or composition of the liposome, such as antioxidants, cryoprotectants, etc. The term "consisting essentially" of is used to define a substance, e.g. liposome, that includes the recited constituents but excludes other constituents that may have an essential significant effect on a parameter of the liposomes, the stability, release or lack of release of the agent from the liposome as well as on other parameters characterizing the liposomes); "consisting of" shall thus mean excluding more than trace amounts of such other constituents. Embodiments defined by each of these transition terms are within the scope of this invention.

Further, all numerical values, e.g. when referring the amounts or ranges of the elements constituting the composition or liposome components, are approximations which are varied (+) or (−) by up to 20 percent, at times by up to 10 percent from the stated values. It is to be understood, even if not always explicitly stated, that all numerical designations are preceded by the term "about". It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Although the invention has been described in conjunction with specific embodiments thereof, it is evident that many alternatives, modifications and variations will be apparent to those skilled in the art, and it is explicitly intended that the invention include such alternatives, modifications and variations.

All publications, patents and patent applications mentioned in this specification are herein incorporated in their entirety by reference into the specification.

DETAILED DESCRIPTION OF SOME NON-LIMITING EXAMPLES

EXAMPLE 1

Liposomes Formulation, Cell Uptake and Cytotoxicity

Materials

Hydrogenated soybean phosphatidyl-choline (HSPC) (Lipoid, Germany)

mPEG (2000)-DSPE (Bio-lab, Jerusalem, Israel);
Folate-PEG(3350)-DSPE (Shaare Zedek Experimental Oncology Lab, Israel)
Cholesterol (Sigma, St. Louis, Mo.)
Alendronic Acid (ALD, Teva, Israel)
Radioactive 3H—Sodium Alendronate (Moravek, Calif., U.S.A)
Doxil (Janssen Pharmaceuticals, NJ, USA)
Doxorubicin (DOX, Teva, Israel)
BALB/c mice (Harlan, Israel)
KB and KB-HiFR, human carcinoma expressing high folate receptor (FR) (Shaare Zedek Experimental Oncology Lab, Israel).
IGROV-1-human ovarian carcinoma expressing high FR (Shaare Zedek Experimental Oncology Lab, Israel).
M109R mouse lung carcinoma (Shaare Zedek Experimental Oncology Lab, Israel)

Methods

Liposomal Formulation:

Liposome formation was performed by standard methods of lipid lyophilization, hydration and polycarbonate membrane extrusion down to 0.1, 0.08, or 0.05-μm pore size. The method in brief is as follows: the lipids used were fully hydrogenated soybean phosphatidyl-choline (HSPC) or mPEG (2000)-DSPE ($^{2000}$PEG-DSPE), and cholesterol. The lipid components at the following mole ratios: 53-55% HSPC, 40% cholesterol, and 5-7% $^{2000}$PEG-DSPE, were weighed, dissolved in tertiary-butanol, frozen in liquid nitrogen and lyophilized overnight. Alternatively, lipids were weighed at the foresaid ratios, dissolved in ethanol, and mixed with hydration buffer to form liposomes.

Encapsulation of Bisphosphonate (Alendronate):

Alendronate (ALD) was encapsulated into the liposomes by rehydration in buffer containing 250 mM ammonium ALD, with pH of about 6. Resuspended liposomes were processed by serial size extrusion in a high-pressure extruder device [Lipex Biomembranes, Vancouver, BC] with temperature control at 60° C. through filters with pore sizes from 1000 nm to 50 nm. Non-encapsulated ALD was removed by dialysis against a buffer of 5% dextrose (or 10% sucrose) with 15 mM histidine, pH 7.0, followed by passage over a Dowex anion exchange resin. The liposomes were sterilized by filtration through 0.22 μM filters and stored in Vacutainer™ tubes at 4° C. A suspension of small unilamellar liposomes of ~100 nm diameter was obtained.

Phospholipid and ALD content were determined after Folch extraction (8:4:3 chloroform:methanol:DDW or sample) (Shmeeda, H., Even-Chen, S., Honen, R., Cohen, R., Weintraub, C., and Barenholz, Y. Enzymatic assays for quality control and pharmacokinetics of liposome formulations: comparison with nonenzymatic conventional methodologies. Methods Enzymol, 367: 272-292, 2003), to separate phospholipids (lower phase), from ALD (upper phase). Samples of each phase were assayed by the Bartlett method to determine phosphorus.

Encapsulation of Amphipathic Weak Base Drug (Doxorubicin):

Liposomes containing the ALD (L-ALD), prepared as described above) were incubated with doxorubicin (DOX) at a DOX-ALD molar ratio of 0.5, for 60 min at a temperature of 60° C. and cooled immediately. The resulting liposome suspension was passed through a Dowex cation exchange resin to remove any non-encapsulated DOX. The formulation was sterilized using 0.45 μm or 0.22 μm filters. The final concentration of DOX in the formulation was adjusted to 2.0 mg/ml by further dilution with the foresaid dialysis buffer.

Characterization of the Co-Encapsulating Liposomes:

Doxorubicin absorbance was measured spectrophotometrically at 480 nm wavelength after extraction from liposomes in acidified tertiary butanol. Final phospholipid and ALD were re-quantified as described above.

The resulting liposomes contained a ALD:DOX (L-ALD/DOX) molar:ratio of ~1.5 (or DOX/ALD molar ratio of ~0.7). The particle size of the co-encapsulated liposomes was between 70-120 nm (diameter), determined by dynamic light scattering (DLS) of a 20 µl sample diluted in 1.0 ml of saline using a Malvern Particle Analyzer.

Encapsulation Efficiency and Stability Assessment:

To determine whether there was any residual free drug (DOX or ALD) and to follow encapsulation stability, gel chromatography fractionation was used to separate liposomal material from non-encapsulated, low molecular weight material. A sample of liposomes was passed through a column of Sepharose-6G, and 20 one-ml fractions were collected. A spike of [3H]-radiolabeled sodium ALD was added to ammonium ALD in a test formulation thus enabling their follow-up by scintillation counting of fraction samples (20 µl) extracted in acidified isopropanol (1:10). DOX was measured either spectrophometrically at 480 nm, or by fluorescence emission at 590 nm with excitation at 470 nm after extraction in acidified isopropanol (1:10). Phospholipid concentration was determined on 50 µl samples by the modified method of Bartlett (Shmeeda et al., 2003, as described above).

Plasma stability was assessed by incubation of 100 µl of liposomes with 400 µl of human plasma at 37° C. for up to 24 h and assessed for release of ALD and DOX as above.

Cell Uptake and Cytotoxicity:

The cytotoxicity of L-ALD/DOX relative to DOXIL and other control samples (free DOX, free ALD and L-ALD) was determined in three human cell lines, KB human cervical carcinoma, N87 human gastric carcinoma cells and IGROV-1 ovarian carcinoma.

Cytotoxicity was assayed using varying concentrations of ALD (0.1-200 µM) under standard 72 hr, continuous exposure, in 96-multiwell assays. Growth rate was assessed colorimetrically based on methylene blue staining and data was obtained with an automatic plate reader and IC50 values were determined The uptake of DOX from L-ALD/DOX was compared to that of Doxil in KB cells incubated for 3 h at 37° C. with 5 µg/ml of each formulation based on Doxorubicin concentration.

Plasma Levels of Doxorubicin in Mice:

BALB/c mice were injected i.v. with 100 µg doxorubicin either as L-ALD/DOX formulation (as described above) or as a commercial formulation of liposomal doxorubicin known as Doxil™. Blood was drawn from mice 24 hours later and plasma levels of doxorubicin were measured fluorimetrically after extraction of doxorubicin from plasma (100 µl of plasma are extracted in 900 µl of acidified isopropanol). Doxorubicin concentration was measured fluorimetrically using an excitation wavelength of 470 nm and emission wavelength of 590 nm as previously described (Gabizon et al., Clin Cancer Res 2003).

Therapeutic Study in BALB/c Mice:

Mice (~8-10 week old female BALB/c) were purchased from Harlan Breeding Laboratories (Jerusalem, Israel) All animal experiments were done under a protocol approved by the Hebrew University-Hadassah Institutional Review Board for use of animals in research. The tumor model used here is the mouse M109R (doxorubicin resistant) carcinoma. M109R tumor cells ($10^6$ cells/0.05 ml) were inoculated into the subcutaneous space of the mouse right hind footpad.

Five to 7 days after inoculation, mice injected with M109R cells developed solid tumors as measured by the increased thickening of the footpad. Different liposomes were injected i.v. at dose levels of 5 mg/kg based on Doxorubicin content or an amount of Alendronate equivalent to that present in the co-encapsulated formulation at doxorubicin dose of 5 mg/kg. The dose selected for the co-encapsulated L-ALD/DOX was well tolerated. The following groups were compared in two sets of experiments: (i) Untreated, (ii) Doxil, (iii) L-ALD/DOX and (iv) combination of two liposomal formulations, L-ALD+Doxil. Treatment was administered on Day 7 (D7), Day 14 (D14) and Day 21 (D21). Kaplan-Meyer curves were based on an experimental endpoint of tumor size equal or greater than 4 mm.

Results

Liposomal Formulation:

A shown in Tables 2A, 2B and 2C below the final preparation contains between 3 to 4 micromoles of ALD and ~30 micromoles of phospholipid.

The content of a typical preparation of a liposome co-encapsulated with bisphosphonate, such as ALD and doxorubicin was determined to be as follows:

Phospholipid (PL) concentration ~30 µmol/ml,
Final bisphosphonate concentration of ~1 mg/ml with a ALD/PL mole ratio of ~0.10.
Final doxorubicin concentration of ~2 mg/ml with Doxorubicin/PL molar ratio of ~0.05;
ALD/DOX molar ratio of ~2.
Average particle size of 70-120 nm (for extruded liposomes).

TABLE 2A

Alendronic liposomes before DOX loading

| # Batch | ALD Concentration | | | PL Concentration | | |
|---|---|---|---|---|---|---|
| | µmol/ml | mg/ml | % recovery | µmol/ml | mg/ml | % recovery |
| 293 | 7.05 | 2.29 | 4.9 | 21.65 | 16.9 | 63 |
| 294 | 6.8 | 2.21 | 4.76 | 24.5 | 19.1 | 71.5 |

TABLE 2B

Liposomes after DOX loading

| # Batch | ALD Concentration | | PL Concentration | | DOX Concentration | | |
|---|---|---|---|---|---|---|---|
| | µmol/ml | mg/ml | µmol/ml | mg/ml | µmol/ml | mg/ml | % recovery |
| 293 | 6.9 | 2 | 18.8 | 14.7 | 2.8 | 1.67 | 80 |
| 294 | 6.5 | 1.9 | 18.4 | 14.4 | 2.44 | 1.44 | 88.3 |

TABLE 2C liposome characteristics before (Pre) and after (Post) DOX loading

| # Batch | Size (nm) | | pH | | mOsm/L | |
|---|---|---|---|---|---|---|
| | Pre-DOX | Post-DOX | Pre-DOX | Post-DOX | Pre-DOX | Post-DOX |
| 293 | 98.8 | 99.7 | 7 | 7.2 | 305 | 318 |
| 294 | 96.6 | 98.7 | 7 | 7.5 | 252 | 277 |

Co-encapsulation of ALD and DOX (L-ALD/DOX) was validated using gel chromatography fractionation in order to separate liposome material from low molecular weight material (the non-encapsulated drugs) as described in methods. FIGS. 2A-2D show, using a formulation containing a trace of radiolabeled alendronate, at which fractions L-ALD/DOX elute.

Figure 2A:
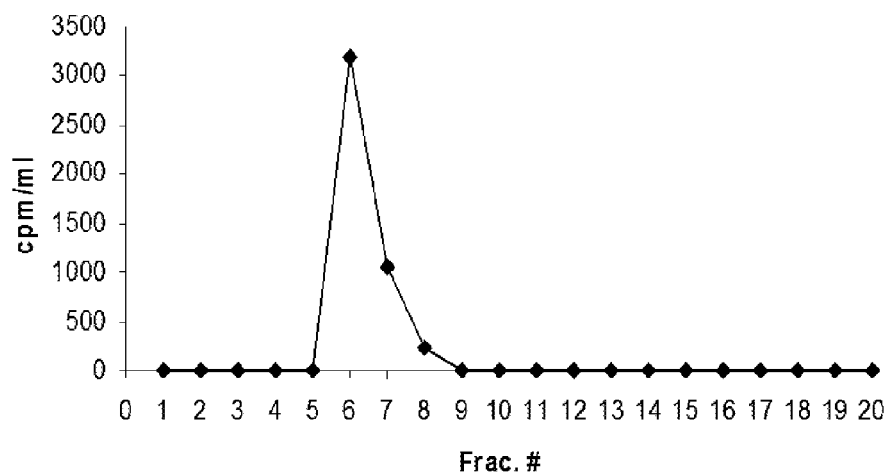
FIGS. 2A-2B are chromatographic separation graphs, showing that alendronate (ALD) was eluted with the liposome fractions (#5-#7), whereas later fractions (#9-#12), where proteins and small molecules are found, contained negligible amounts of free drug (FIG. 2A) and that doxorubicin (DOX) was eluted with the liposome fractions (#5-#7) and later fractions (#9-#12) contained negligible amounts of free drug (FIG. 2B)

As shown in FIG. 2A, the radiolabeled ALD was eluted with the liposome fractions (#5-#7) and later fractions contained negligible amounts of ALD.

Figure 2B:
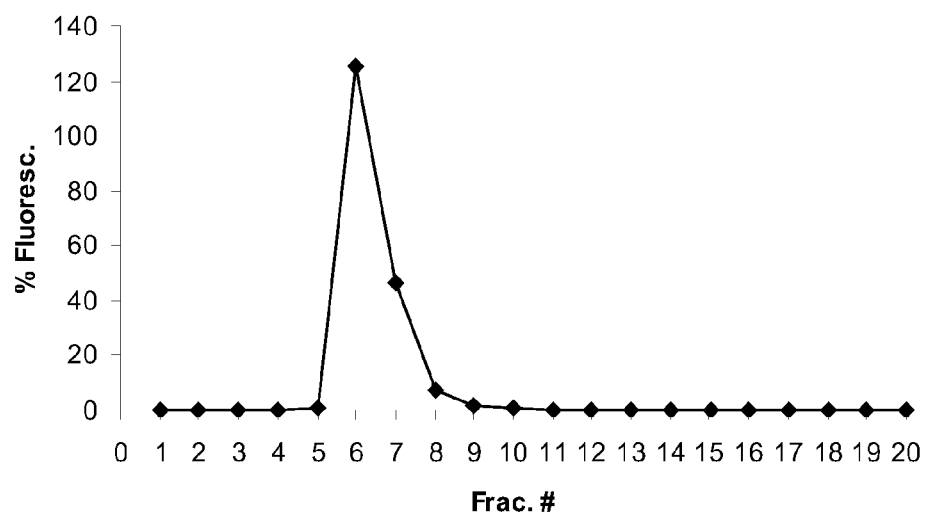

In addition, as shown in FIG. 2B, doxorubicin was eluted with the liposome fractions (#5-#7) and later fractions contained negligible amounts of drug.

It is importantly noted that the patterns of elution of both drugs (ALD and DOX) overlap with each other confirming indeed that they are co-encapsulated in the same liposome. Using this technique, liposome-associated drugs were previously found to elute in fractions #5-#7, while free, non-encapsulated drugs eluted in fractions #10-#12.

Figure 2C:
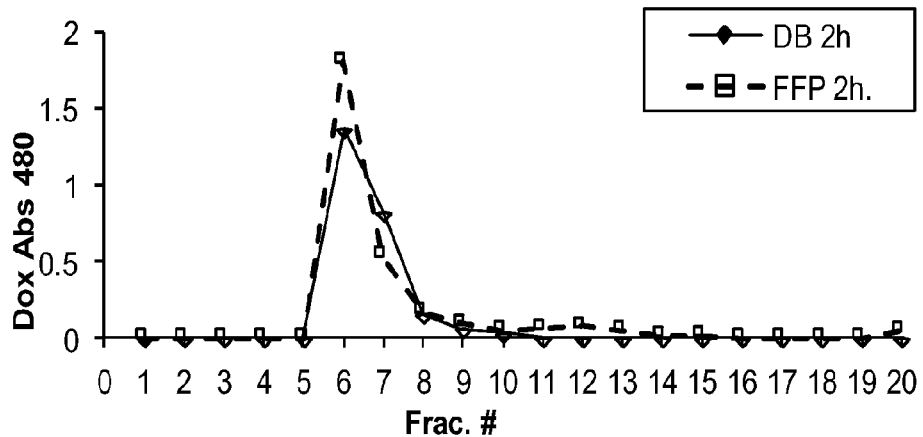
FIGS. 2C-2D are chromatographic separation graphs based on spectrophotometric measurements of doxorubicin at 480 nm demonstrating the stability of the L(liposomal)-ALD/DOX after 2 h (FIG. 2C) and 24 h (FIG. 2D) exposure to buffer (DB) or human fresh frozen plasma (FFP), and which show complete liposome retention of DOX by chromatographic separation of the co-encapsulated drugs (fractions #5-7) from any free or protein-bound drugs (fractions #9-12).
Figure 2D:
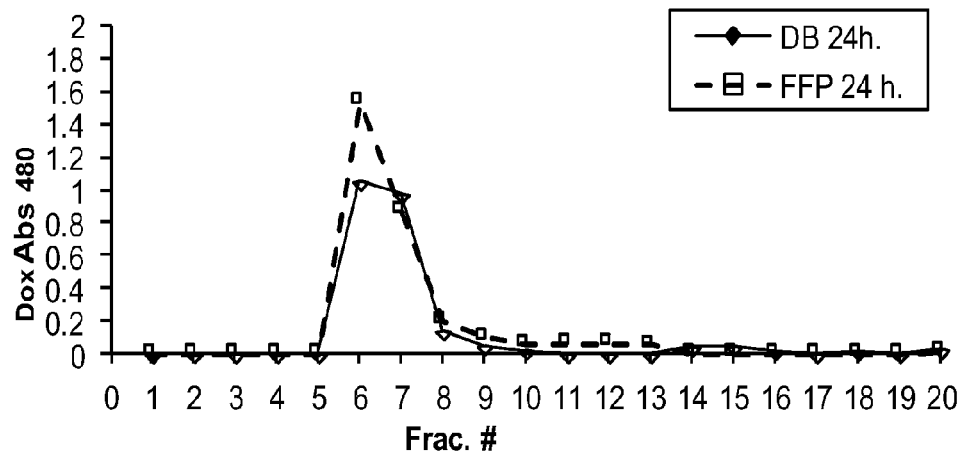

Further, as shown in FIGS. 2C and 2D, the stability of the L-ALD/DOX after 2 h and 24 h exposure to human plasma demonstrates complete retention of DOX within liposomes under these conditions.

Figure 3A:
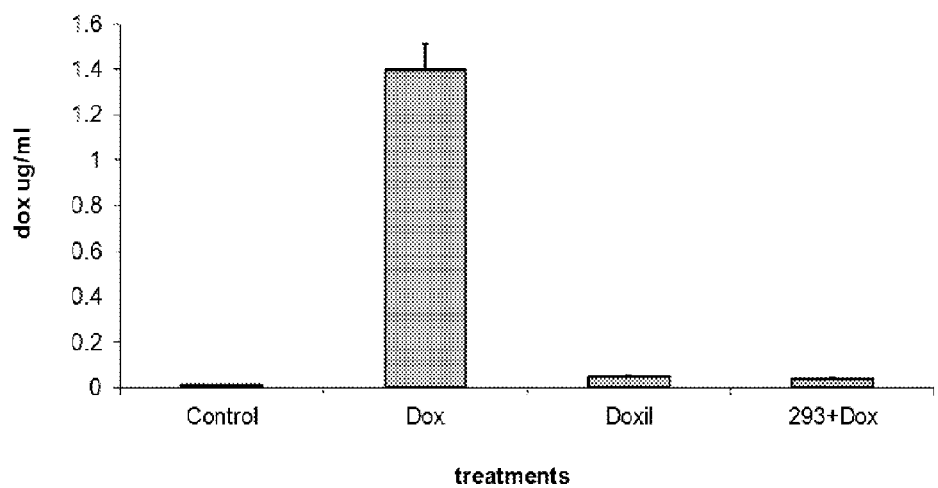
FIGS. 3A-3D are in vitro cell uptake (FIG. 3A) and cytotoxicity studies (FIGS. 3B-3D) of free agents (DOX and ALD), Doxil (liposomal doxorubicin sulfate), liposomal ALD (L-ALD), and liposomal ALD and DOX (L-ALD/DOX) in cancer cells, specifically.
Figure 3B:
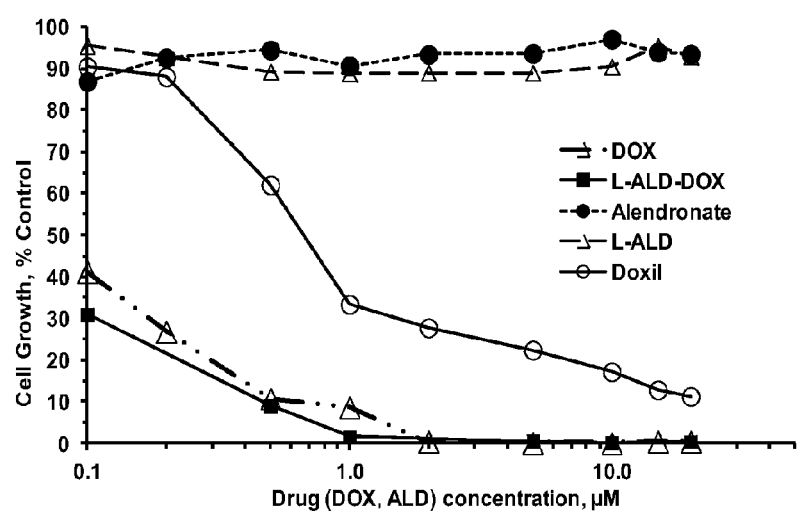
Figure 3C:
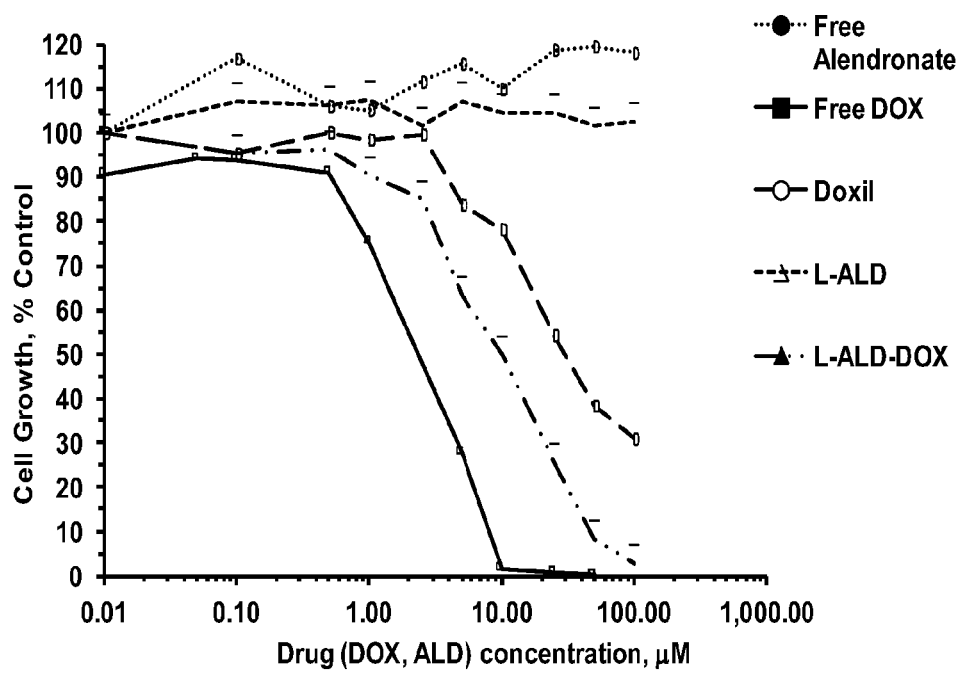
Figure 3D:
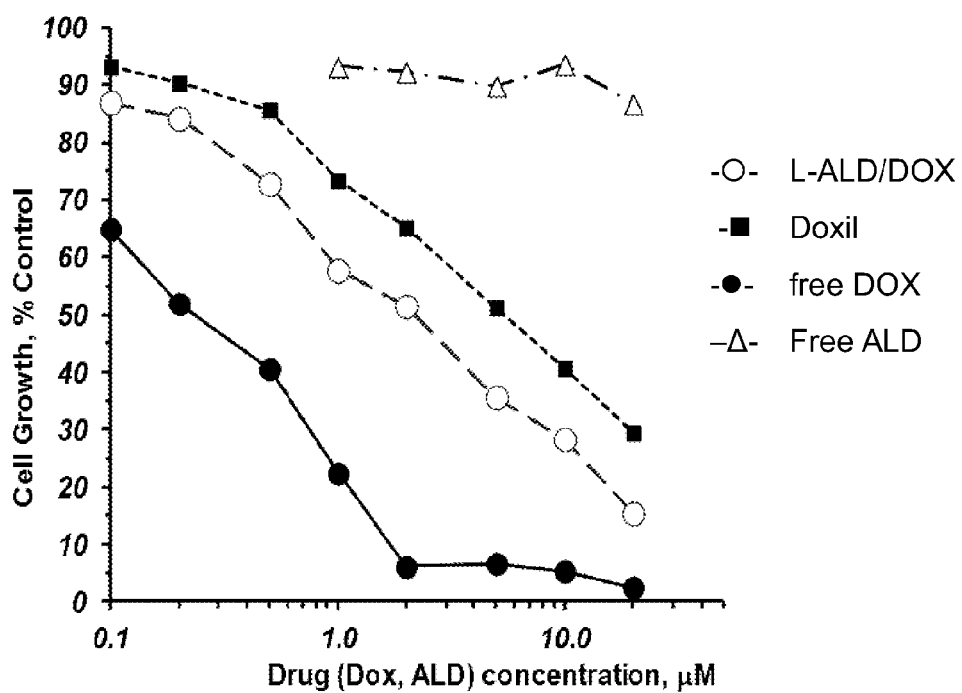

Cytotoxicity & Cellular Uptake:

Cellular uptake in KB cells of free DOX, Doxil and L-ALD/DOX was compared (FIG. 3A). Specifically, exposure of KB tumor cells to pegylated liposomal L-ALD-DOX, shows equally low cell uptake of doxorubicin (Dox) when compared to Doxil, indicating that the greater cytotoxicity of the former cannot be explained by a greater exposure to doxorubicin, and is necessarily related to the combined presence of ALD and DOX in the same liposome In addition, the cytoxicity of free ALD, L-ALD and L-ALD/DOX were compared to that of free DOX and Doxil in KB (FIG. 3B), N87 (FIG. 3C) and IGROV (FIG. 3D) cell lines. L-ALD/DOX was more cytotoxic than Doxil and remarkably approximates the activity of free DOX. Note, L-ALD and free ALD have essentially no cytotoxicity in these cell lines.

It is noted that non-targeted liposome formulations generally show inferior in vitro cytotoxicity to that of the free drug control. IC50 values are also shown in Table 3.

TABLE 3

| | (IC-50 in µM): | | |
|---|---|---|---|
| Treatment | KB-hiFR | N-87 | IGROV |
| Free ALD | >20 | >100 | >20 |
| Free DOX | 0.04 | 3.12 | 0.25 |
| Doxil | 0.71 | 31.72 | 5.56 |
| Lip-ALD | >20 | >100 | >20 |
| Lip-ALD/DOX | 0.36 | 9.95 | 2.28 |
| FT-Doxil | 0.42 | | |
| FT-L-ALD | >20 | | |
| FT-L-ALD/DOX | 0.1 | | |

DOX cellular uptake with L-ALD/DOX was low and similar to that of Doxil uptake. Therefore the greater cytotoxicity of L-ALD/DOX cannot be explained by greater DOX delivery indicating a significant cytotoxic contribution of the co-encapsulated combination of ALD and DOX (namely same uptake but greater cytotoxicity).

Figure 4A:
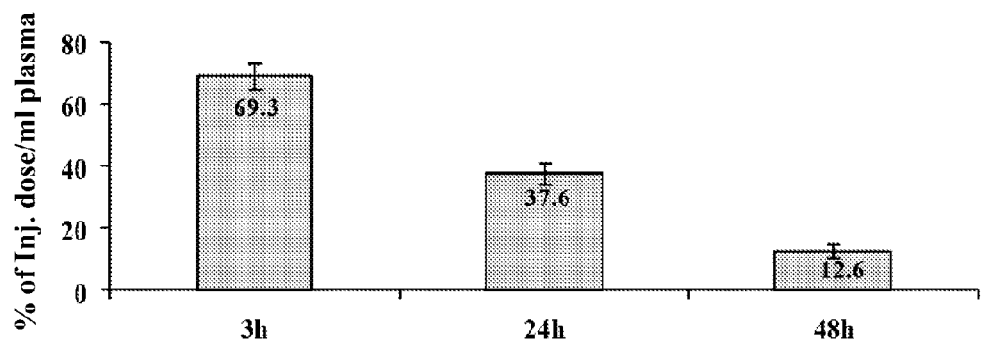
FIGS. 4A-4C show pharmacokinetics of L-ALD/DOX based on doxorubicin concentration in plasma, FIG. 4A demonstrating the pharmacokinetics of L-ALD/DOX in blood samples that were collected at 3 h, 24 h and 48 h.
Figure 4B:
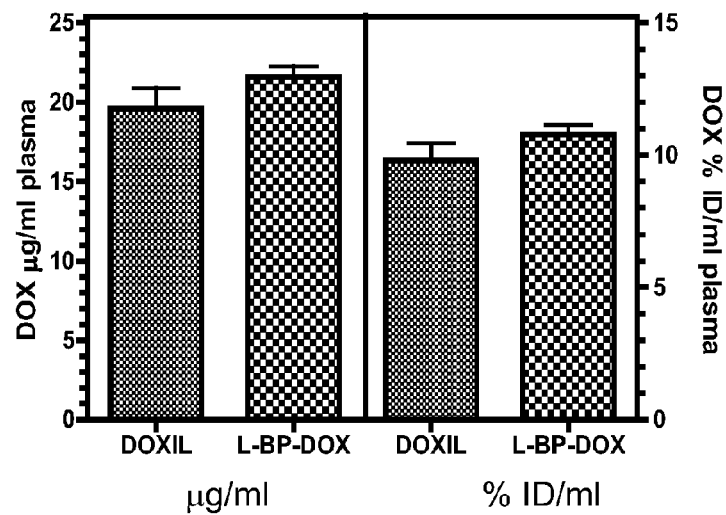
Figure 4C:
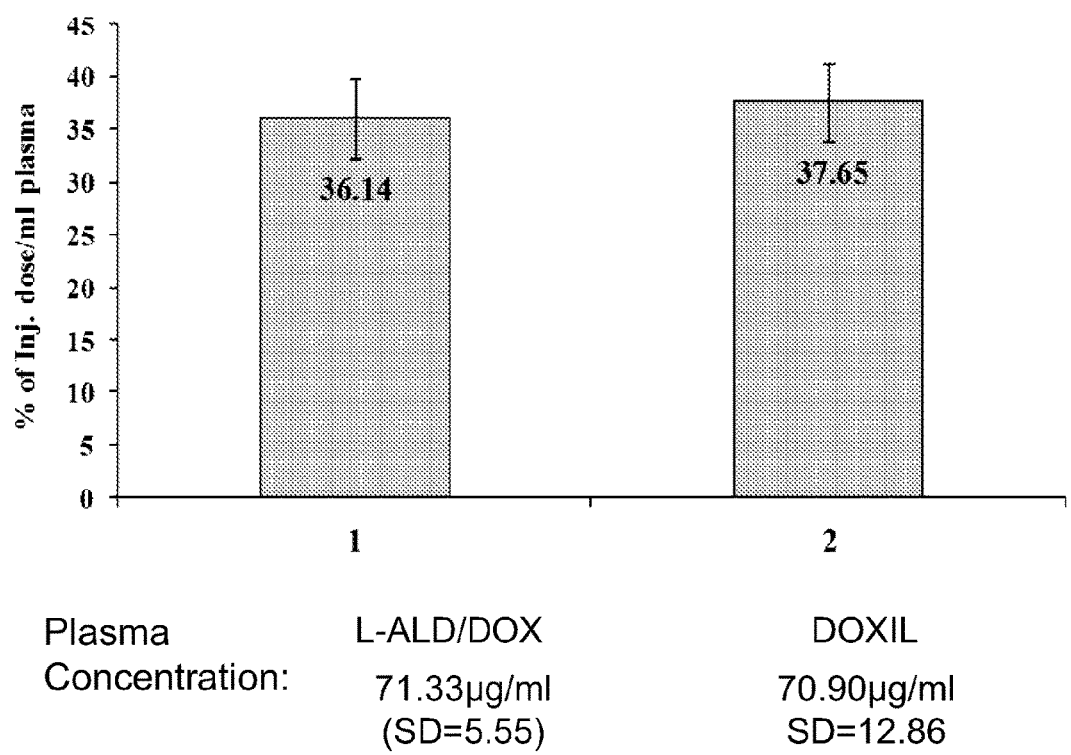

Plasma Levels of Doxorubicin in Mice:

The results presented in FIG. 4A demonstrate the pharmacokinetics of L-ALD/DOX based on doxorubicin concentration in plasma measured after 3 h, 24 h and 48 h. The results shown in FIGS. 4B-4C indicate that upon administration of Doxil or L-ALD/DOX, similar high doxorubicin levels were present in the plasma of mice 24 hr after i.v. injection of these liposomal formulations in the tail vein of Sabra mice. This indicates that the co-encapsulated liposomal formulation L-ALD/DOX according to the invention, and in this particular example, was stable and exhibited a long-circulating time (20% of the injected dose at 24 h) in vivo.

Therapeutic Results

Figure 5A:
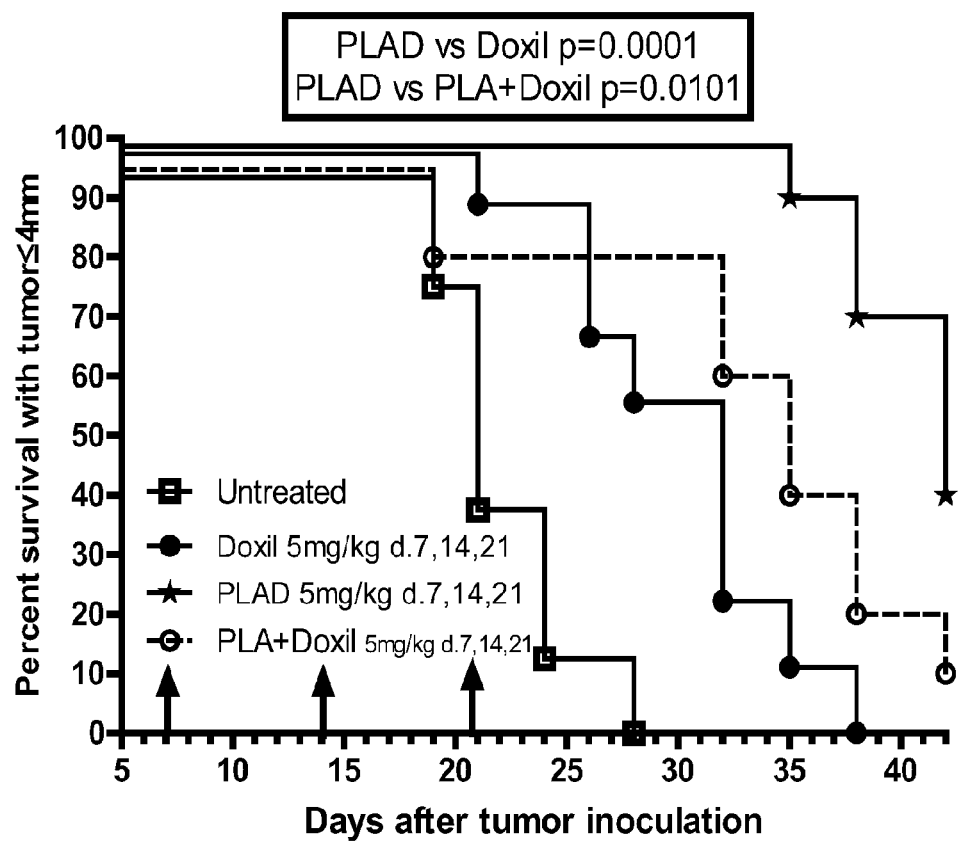
FIGS. 5A-5D present results of in vivo studies with doxorubicin resistant mouse lung tumor cells, M109R.
Figure 5B:
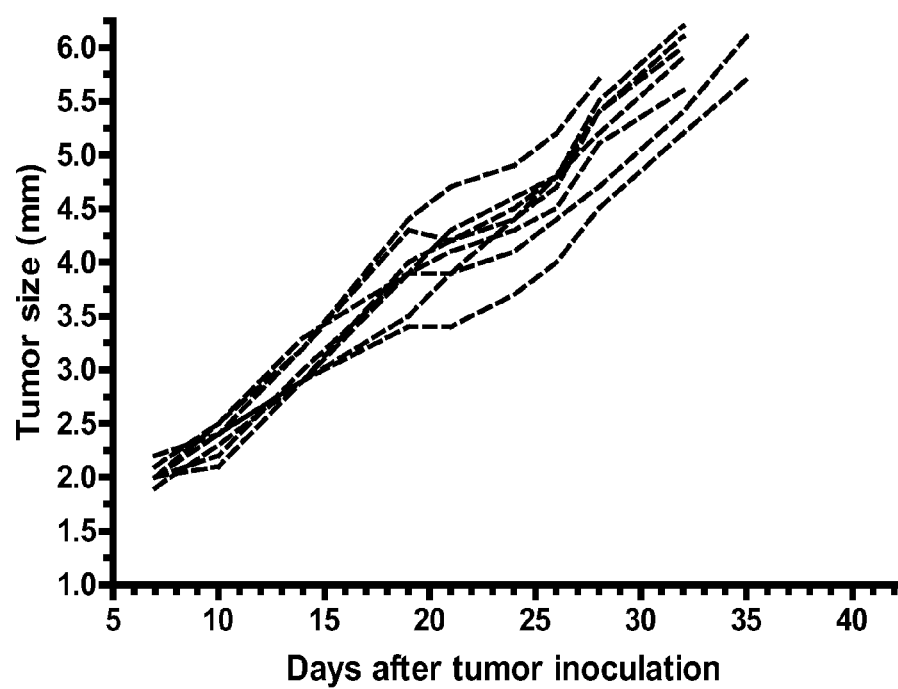
Figure 5C:
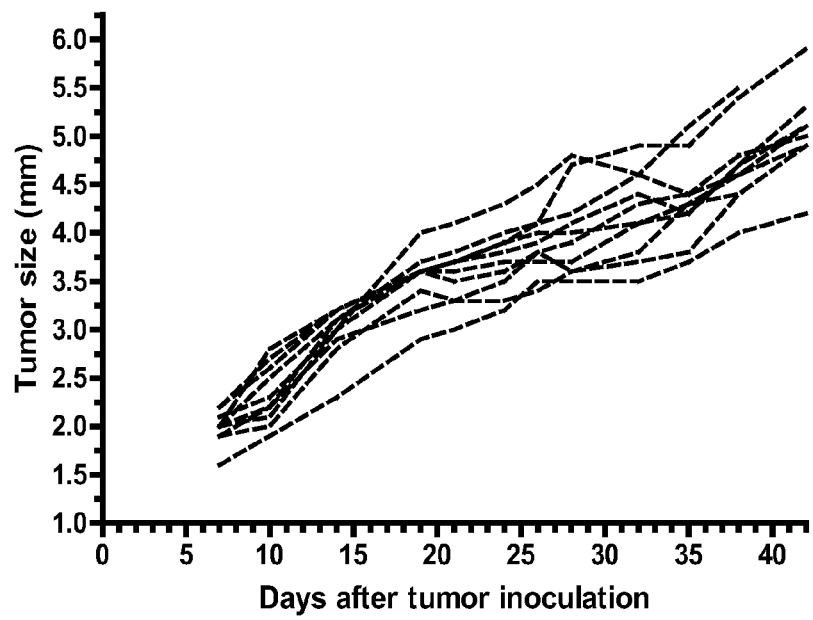
Figure 5D:
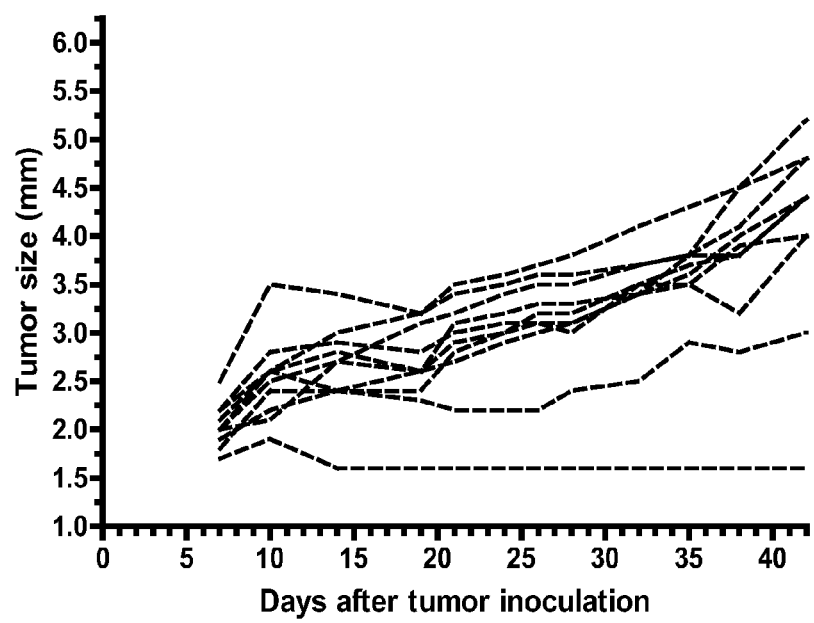

The results presented in FIGS. 5A and 5B-5D relating to M109R tumor model (a tumor relatively resistant to doxorubicin) demonstrate the significant increase of anti-tumor activity of L-ALD/DOX (presented in FIG. 5A as PLAD) when compared to Doxil. FIG. 5A shows the survival curves of mice inoculated with M109R and subsequently, after tumor establishment, treated with either 5 mg/kg Doxil or L-ALD/DOX. The graph demonstrates increased anti-tumor activity of L-ALD/DOX (PLAD) in M109R tumor (relatively resistant to doxorubicin) compared to Doxil. It is noted that L-ALD and free ALD had no anti-tumor effect (data not shown). L-ALD/DOX was also significantly more active in vivo than a combination of Doxil and L-ALD (FIG. 5B). L-ALD alone was inactive (ALD in L-ALD was given at the same dose as ALD in L-ALD/DOX). Looking at individual tumor growth curves (FIG. 5C) from which previous Figures were derived, the experiment shows that L-ALD/DOX is clearly more effective than Doxil.

EXAMPLE 2

Encapsulation of Alendronate and Doxorubicin in Folate Targeted Liposomes

Methods

Liposomal Formulation and Alendronate Encapsulation:

Liposome formulation and bisphosphonate encapsulation and gradient loading of doxorubicin were performed by standard methods as described in Example 1.

Folate Receptor Targeted Liposomes:

Folate-derivatized $^{3350}$PEG-DSPE was synthesized as described by Gabizon et al. (Gabizon A, Horowitz A, Goren D, Tzemach D, Mandelbaum-Shavit F, Qazen M, and Zalipsky, S. *Targeting folate receptor with folate linked to extremities of poly(ethylene glycol)-grafted liposomes: in vitro studies*. Bioconjugate Chemistry 10 (2):289-98, 1999). In brief, the procedure includes the following: Folic acid dissolved in anhydrous DMSO is added to amino-$^{3350}$PEG-DSPE in pyridine containing dicyclohexylcarbodiimide (DCC). The mixture is incubated in the dark for 4 hr at RT with stirring. A white precipitate forms: dicyclohexylurea (DCU), a secondary by-product. The supernatant is yellow, containing free, non-reacted folate and folate-$^{3350}$PEG-DSPE. The reaction is followed by TLC (see below) based on the disappearance of amino-PEG-DSPE by staining with ninhydrin and the appearance of a new yellow spot—folate-$^{2000}$PEG-DSPE. TLC Mobile phase: chloroform/methanol (75:36) run on TLC Silica gel 60 F254 sheets. The reaction mixture is centrifuged at 3000 rpm 2 min, the supernatant removed to a new vial. Pyridine in the supernatant is removed the by rotary evaporation. DDW is added until totally dissolved and then the supernatant is dialyzed in Spectra/Por Membrane MWCO: 50000 dialysis tubing against saline and then DDW to remove DMSO, free folate and remnants of pyridine. The dialysate is lyophilized and a sample is taken for HPLC analysis using a Phenomenex Prodigy 5µ, C8 (100×4.6 mm) Column in a mobile phase composed of: methanol/10 mM sodium phosphate pH 7.0 (92:8 v/v) at a flow rate of 1 ml/min, RT, detection λ of 285 nm. The Retention Time of free Folate is 0.8 min, and that of Folate-PEG-DSPE is 2.5 min.

The Folate-$^{3350}$PEG-DSPE (MW=3232) was incubated with pre-formed liposomes containing either ALD alone or the co-encapsulated ALD-DOX liposomes at 0.1-0.5% of the total phospholipid content of the liposomal formulation as determined by Bartlett (see methods Example 1). Specifically, the Folate-$^{3350}$PEG-DSPE was added as a dry powder to the liposomes containing drug/drugs and incubated at 45° C. for 2 hrs while shaking. Then, liposomes were centrifuged (10 min, 3000 rpm) to remove any non-incorporated Folate-$^{3350}$PEG-DSPE which precipitates because of its insolubility in water.

Folate-$^{3350}$PEG-DSPE liposome content was determined spectrophotometrically at 284 nm as described previously (Gabizon et al., 1999, ibid.) or by HPLC (92% methanol/8% 10 mM sodium phosphate buffer pH 7.0), at wavelength 285 nm, RT 3.0 min.

Cytotoxicity & Cellular Uptake:

The cytotoxicity of Folate-targeted co-encapsulated L-ALD/DOX, as well as the cytotoxicity of Folate-targeted Doxil and Folate-targeted liposomal ALD, were determined on two folate receptor (FR)-upregulated human cell lines, KB cervical carcinoma and in IGROV-1 human ovarian carcinoma. Other controls included Free ALD and DOX.

Cytotoxicity was assayed as described above in Example 1.

The uptake of DOX from Folate-targeted L-ALD/DOX was compared to that of Folate targeted Doxil in KB-HiFR cells incubated for 3 h at 37° C. with 5 µg/ml of each formulation based on Doxorubicin concentration.

Results

Figure 6:
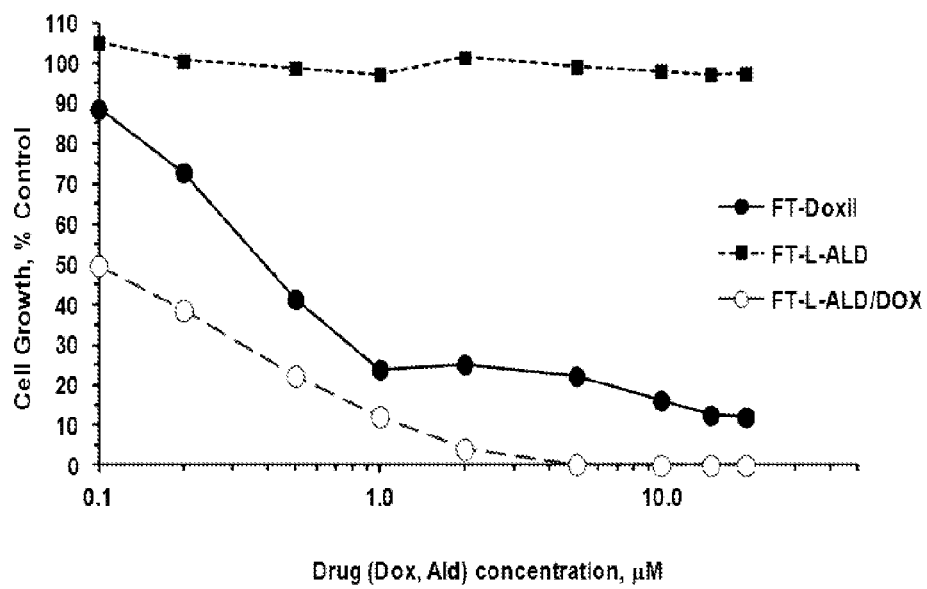
FIG. 6 compares the cytotoxicity effect of the various folate targeted (FT) liposomal formulations: FT-Doxil, FT-L-ALD and FT-L-ALD/DOX, tested in KB-HiFR (human carcinoma with high expression of folate-receptor) cells; the graph shows that the FT-L-ALD/DOX displayed greater cytotoxicity in the KB-HiFR cell line than FT-Doxil whereas FT-L-ALD had no significant activity.

The cytotoxicity of free Alendronate, Folate targeted (FT) L-ALD and FT-L-ALD/DOX were compared to that of free DOX, and FT-Doxil in the FR-upregulated KB human cell line (FIG. 6, Table 3). As shown in FIG. 6, FT-L-ALD/DOX had greater cytotoxic activity than L-ALD/DOX. In FIG. 6/Table 3 both of the folate-targeted formulations had much greater cytotoxicity than the non-targeted formulations and FT-L-ALD/DOX had greater activity in these cells than FT-Doxil whereas FT-L-ALD had no significant activity.

Figure 7:
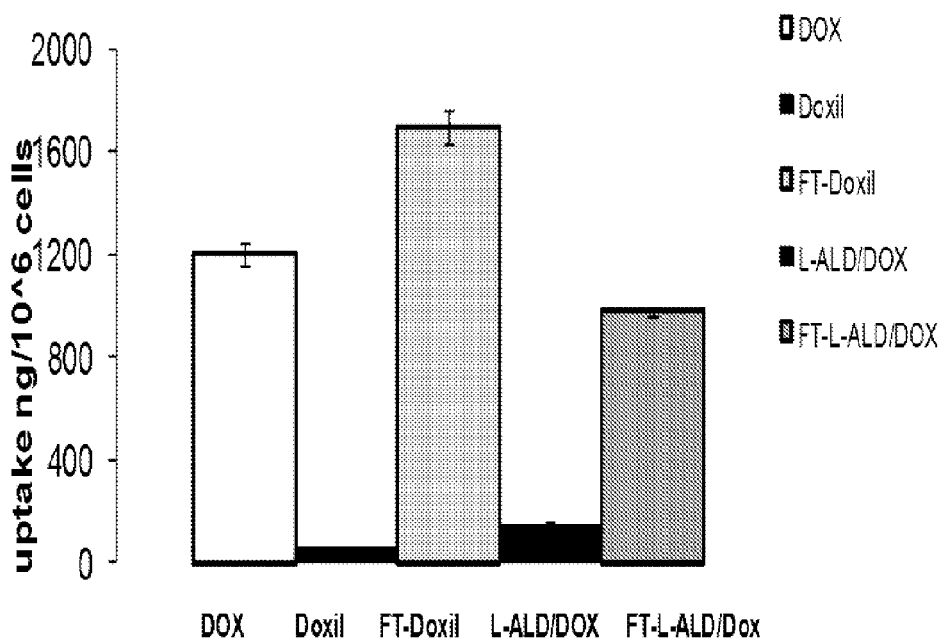
FIG. 7 demonstrates the comparative uptake of doxorubicin in KB-HiFR cells incubated with free DOX, Doxil, FT-Doxil and FT-L-ALD/DOX and non-targeted L-ALD/DOX. The uptake of Dox delivered by folate-targeted (FT) is greater than that of targeted formulations, however, FT-ALD/DOX does not increase delivery of drug to tumor cells over FT-Doxil, and cannot account for its increased cytotoxicity as observed in FIG. 6.

The comparative uptake of doxorubicin after 3 h incubation at 37° C. with the various non-targeted and Folate-targeted formulations was quantified in KB-HiFR cells and the results are displayed in FIG. 7.

While folate-targeted formulations substantially increased uptake of both Doxil and L-ALD/DOX, the uptake of FT-L-ALD/DOX was somewhat lower compared to FT-Doxil. However, if the slightly higher drug-lipid ratio of FT-Doxil is taken into consideration, the lipid mass and hence, the number of liposomes taken up by cells should be considered similar for both formulations (Doxil and L-ALD-DOX in the FT targeted and not targeted versions). Therefore the greater cytotoxicity of L-ALD/DOX cannot be explained by greater DOX delivery indicating a significant cytotoxic contribution of the co-encapsulated combination of ALD and DOX (namely equal or lower uptake but greater cytotoxicity nevertheless).

EXAMPLE 3

Effect of γδ T-Cells on Treatment with Liposomal ALD/DOX in Breast Cancer Cells

Materials

MDA-MB-231, ZR-75, and BT20 breast cancer cells were obtained from the Division of Cancer Studies, Research Oncology Section, Guy's Hospital, KCL School of Medicine, London, UK Methods Three different breast cancer cell lines, MDA-MB-231, ZR-75, and BT20 were plated into 24 well plates in 1 mL of complete media. When cells reached confluency, they were treated according to the following preparations:
(i) 20 µg/mL Liposomal Alendronate (not shown)
(ii) 20 µg/mL liposomal Alendronate/Doxorubicin formulation (PLAD)
(iii) 20 µg/mL of folate targeted (FT)—liposomal Alendronate/Doxorubicin formulation (FT-PLAD)
(iv) 13.3 µg/mL Doxil (this amount is equal to the amount of doxorubicin in PLAD)
(v) drug-free liposome (Stealth liposomes)
(vi) no treatment (Control).

The cells were incubated for 24 h at 37° C. according to the different treatment preparations and after these 24 h, the media with treatment preparations was replaced with fresh complete media or media with $1 \times 10^6$ γδ T-cells and 100 U/mL of IL-2 (used as a growth factor to support viability of theyδ T-cells). This amount of γδ T-cells corresponds to a ratio of approximately 1 tumor cell per 1 γδ T-cell. The cells were then incubated for an additional 24 h.

After the second 24 h period of incubation, the conditional media from the cell different cultures was kept for cytokine analysis and the cell monolayers were stained with crystal violet and the wells photographed for a semiquantitative estimate of the cytolytic-tumoricidal effect of the treatment as described by Wilkie S, et al. (2010) Selective expansion of chimeric antigen receptor-targeted T-cells with potent effector function using interleukin-4. J. Biol. Chem. 285: 25538-44.

The different breast cancer cell lines were also analyzed for their folate expression levels Analysis was done by flow cytometry with a mouse monoclonal anti-human Folate Binding Protein antibody (ABCAM source) and a goat anti-mouse PE secondary antibody.

Results

Figure 8A:
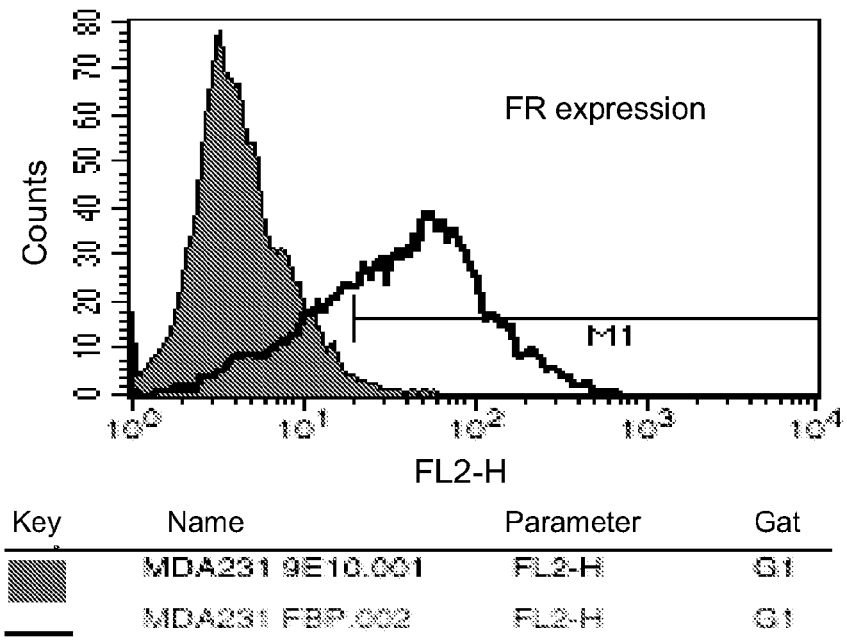
FIGS. 8A-8D present folate expression levels and effect of various formulations on MDA-MB-231 breast cancer cells in the presence or absence of γδ T-Cells; Specifically, FIG. 8A provides flow cytometry of folate expression levels in these breast cancer cells using mouse monoclonal anti-human folate binding protein antibody (ABCAM source) and a goat anti-mouse PE secondary antibody and FIGS. 8B-8D provide images of cells stained with crystal violet to show the effect of liposomal doxorubicin+alendronate (L-ALD/DOX, FIG. 7B), Doxil (FIG. 8C) or folate targeted liposomal doxorubicin+alendronate (FT-ALD/DOX, FIG. 8D), in the presence of γδ T-Cells (+γδ T-cells) or absence of γδ T-Cells (−γδ T-cells).
Figure 8B:
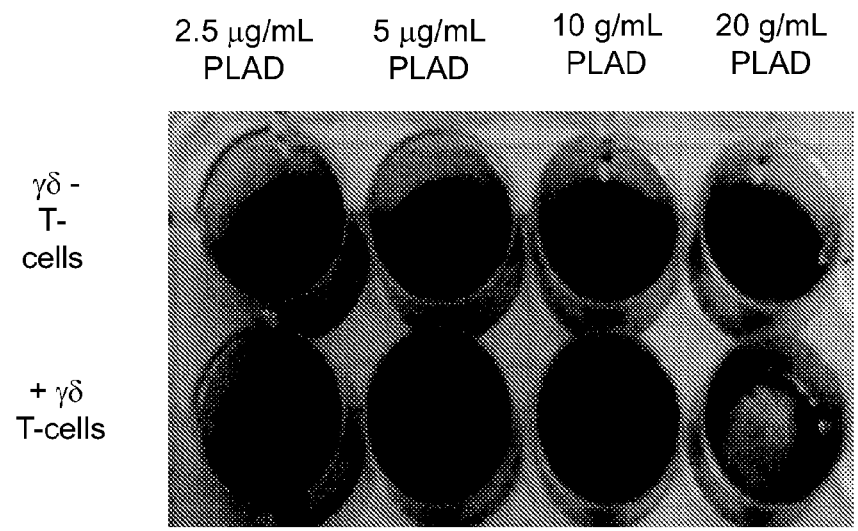
Figure 8C:
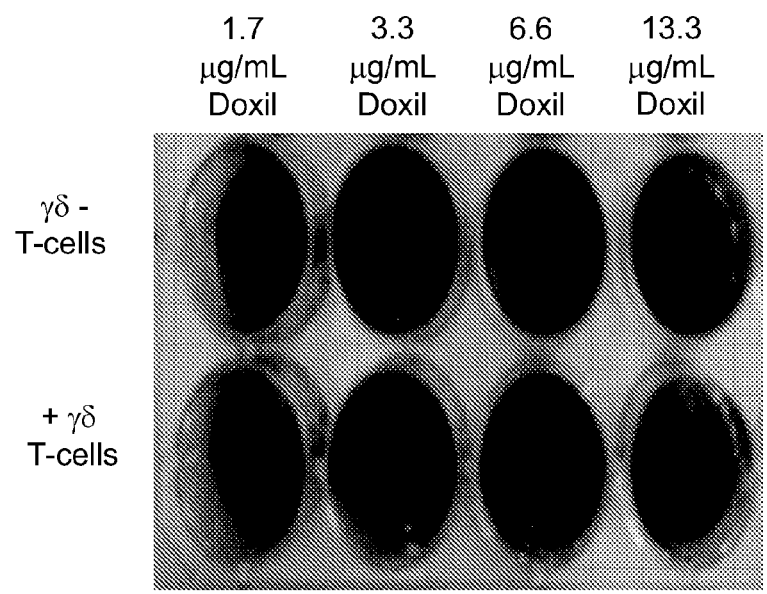
Figure 8D:
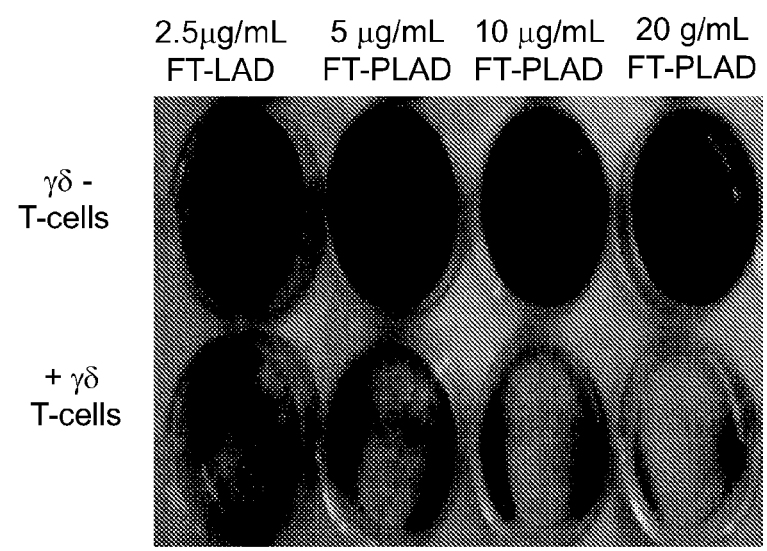
Figure 9A:
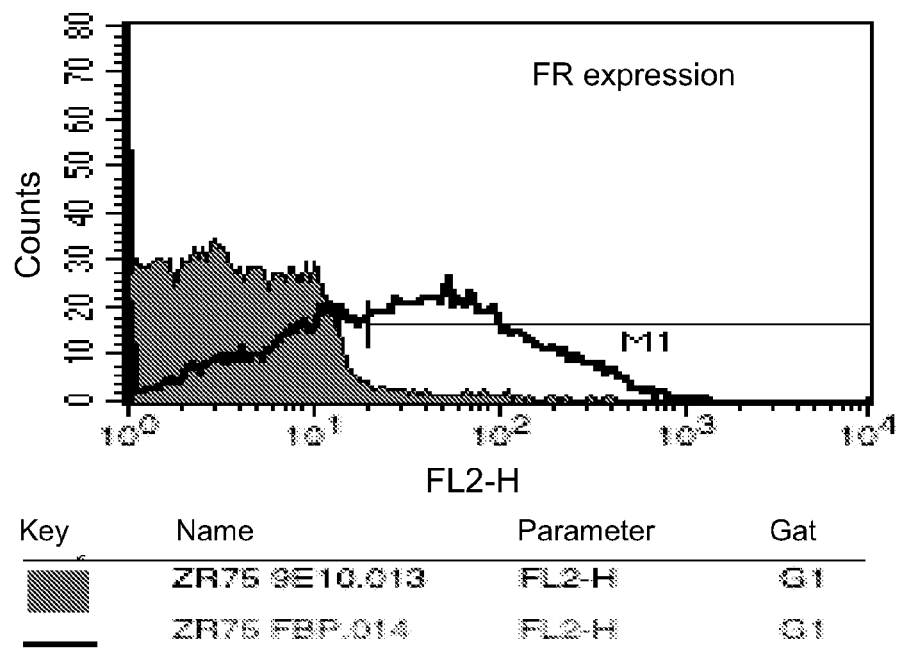
FIGS. 9A-9D present folate expression levels and effect of various formulations on ZR-75 breast cancer cells in the presence or absence of γδ T-Cells; Specifically, FIG. 9A provides flow cytometry of folate expression levels in these breast cancer cells using mouse monoclonal anti-human folate binding protein antibody (ABCAM source) and a goat anti-mouse PE secondary antibody and FIGS. 9B-9D provide images of cells stained with crystal violet to show the effect of liposomal doxorubicin+alendronate (PLAD, FIG. 9B), Doxil (FIG. 9C) or folate targeted liposomal doxorubicin+alendronate (FT-PLAD, FIG. 9D), in the presence of γδ T-Cells (+γδ T-cells) or absence of γδ T-Cells (−γδ T-cells).
Figure 9B:
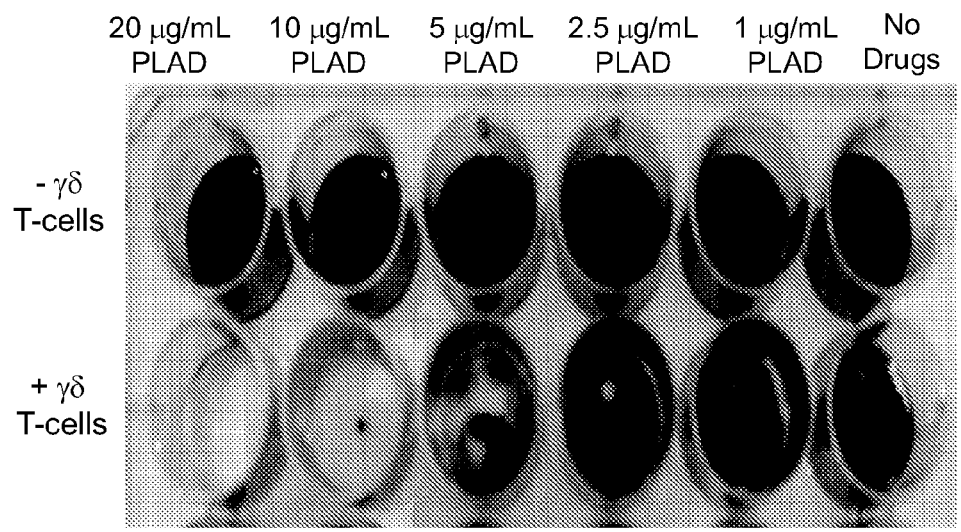
Figure 9C:
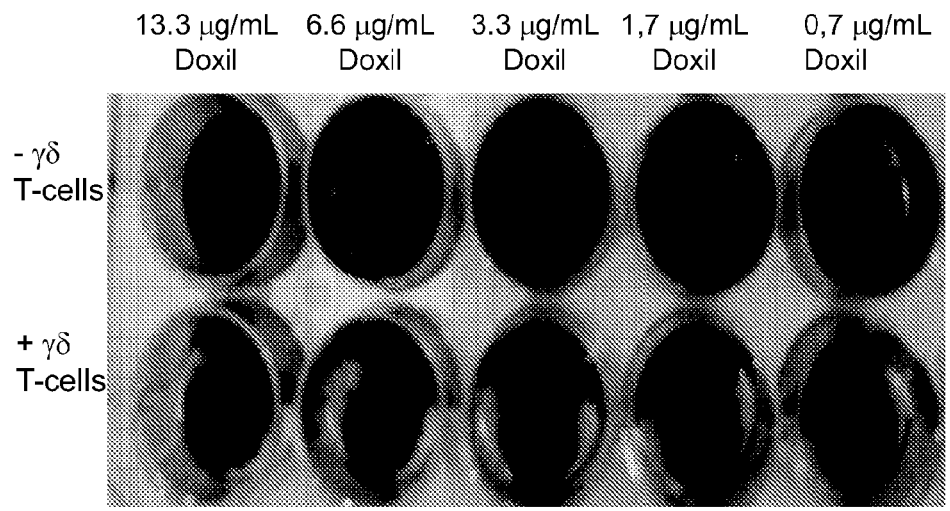
Figure 9D:
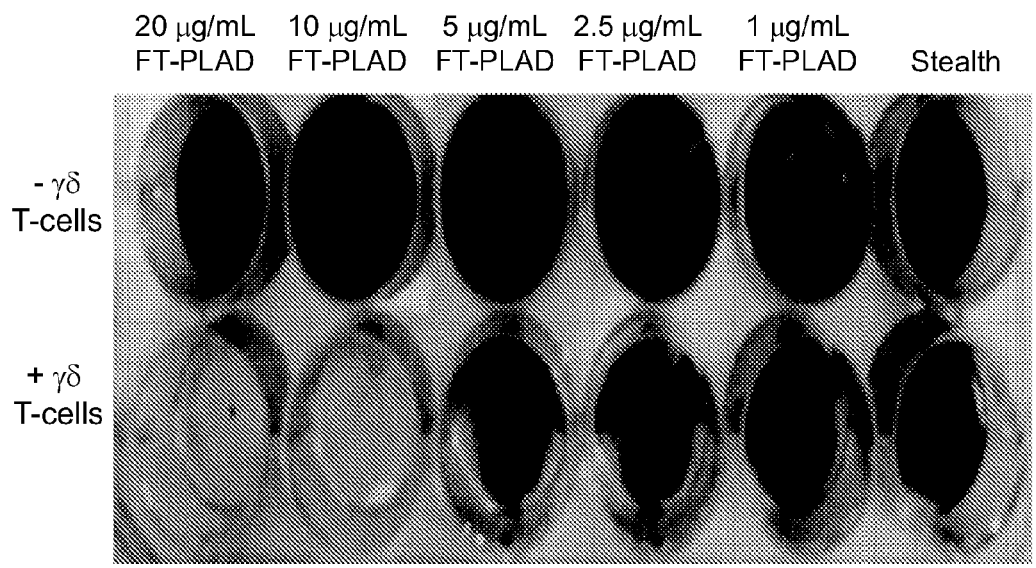
Figure 10A:
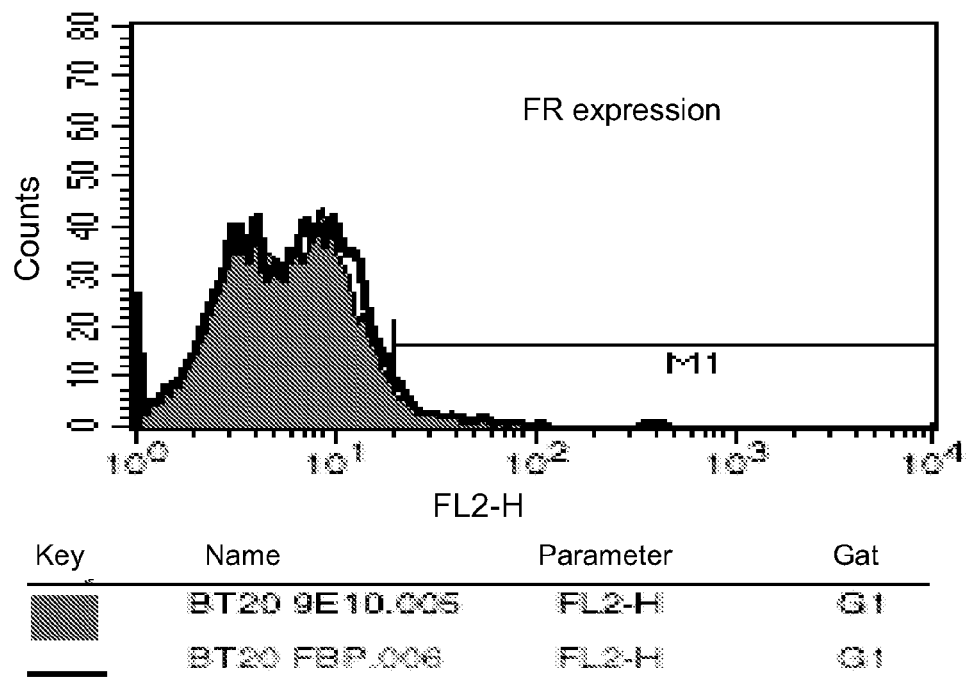
FIGS. 10A-10D present folate expression levels and effect of various formulations on BT20 breast cancer cells in the presence or absence of γδ T-Cells; Specifically, FIG. 10A provides flow cytometry of folate expression levels in these breast cancer cells using mouse monoclonal anti-human folate binding protein antibody (ABCAM source) and a goat anti-mouse PE secondary antibody and FIGS. 10B-10D provide images of cells stained with crystal violet to show the effect of liposomal doxorubicin+alendronate (PLAD, FIG. 10B), Doxil (FIG. 10C) or folate targeted liposomal doxorubicin+alendronate (FT-PLAD, FIG. 10D), in the presence of γδ T-Cells (+γδ T-cells) or absence of γδ T-Cells (−γδ T-cells).
Figure 10B:
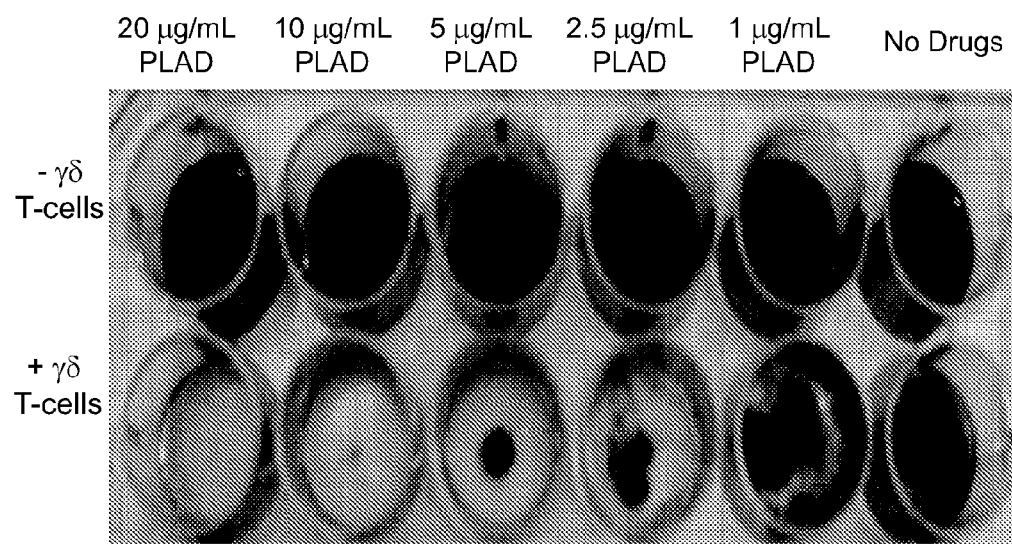
Figure 10C:
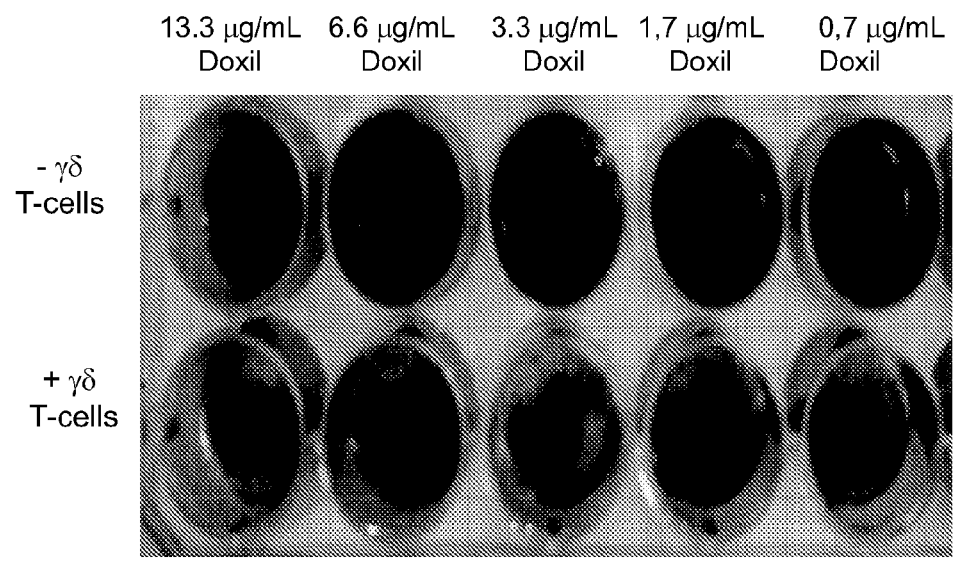
Figure 10D:
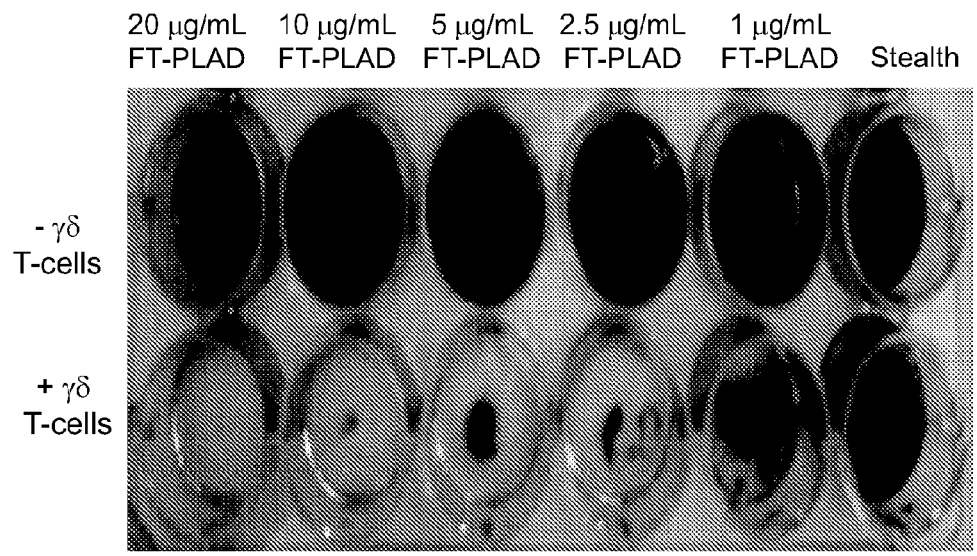

FIGS. 8A, 9A and 10A show that the three lines of breast cancer express the folate receptor. The gap between the unfilled area and the grey filled area indicates the positivity of the cell line expression of the folate receptor (FR) as examined by flow cytometry with anti-folate receptor antibody. The MDA-MB231 and the ZR-75 cell lines are positive for FR. The BT20 cell line is negative for FR.

FIGS. 8B-8D, 9B-9D and 10B-10D show that in the presence of the liposomal ALD/DOX (L-ALD/DOX) the staining was lower as compared to treatment with Doxil only, meaning that the cells were sensitive to treatment and that the cells were even more sensitive when the liposomes were targeted liposomes (FT-L-ALD/DOX).

The results also show that a follow-up treatment with γδ T cells increased the sensitivity of the cells to treatment (exhibited by lower staining), namely, cell death was exhibited to a larger extent.

EXAMPLE 4

Effect of γδ T-Cells on Treatment with Liposomal ALD/DOX in Acute Myeloid Leukemia Cells Materials KG-1 cells [Division of Cancer Studies, Research Oncology Section, Guy's Hospital, KCL School of Medicine, London, UK]

AnnexinV FITC [BD PharMingen, USA]

PKH26 staining was obtained from Sigma.

Methods

The following method is based on the procedure described by Fischer and Mackensen (2003) *The flow cytometric PKH-26 assay for the determination of T-cell mediated cytotoxic activity*. Methods 31: 135-142.

Specifically, $1 \times 10^5$ KG-1 cells, previously stained with PKH26 Red Fluorescent, were plated in a 24 well plate in 1 mL of complete media. These cells were then treated with different preparations:

(i) 20 μg/mL Alendronate (free Alendronate)
(ii) 20 μg/mL of liposomal Alendronate+Doxorubicin (L-ALD/DOX),
(iii) 20 μg/mL of folate targeted liposomal Alendronate+Doxorubicin (FR-L-ALD/DOX);
(iv) 13.3 μg/mL Doxil (the amount of doxorubicin correspondent to doxorubicin in L-ALD/DOX)
(v) Empty liposomes (stealth)
(vi) Control—no treatment.

Cells were incubated for 24 h at 37° C. with a treatment formulation according to the above groups. After 24 h, each group of treated KG-1 cells was co-cultured with γδ T_cells at a ratio of 1 tumor cell to 1 γδ T-cell and at 1 tumor cell to 5 γδ T-cells. In addition, 100 U/mL of IL-2 was also given to each treatment group. Some KG-1 cells were not mixed with γδ T-cells to test for preparation's toxicity.

After 4 h incubation, the cell cultures were stained with AnnexinV FITC (BD) in order to measure the percentage of apoptotic cells. The samples were analysed by flow cytometry and the principle is that tumor cell death is measured by analysing $PKH26^+AnnexinV^+$ cells.

Results

Figure 11:
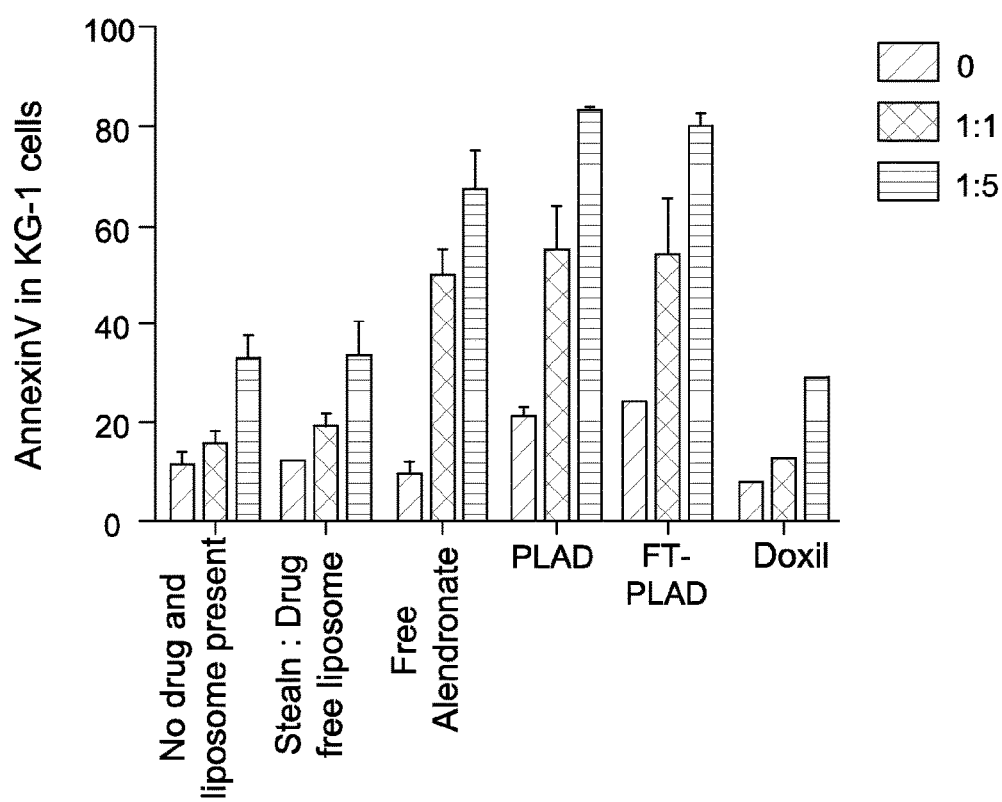
FIG. 11 is a bar graph showing by flow cytometry analysis the level of AnnexinV FITC (BD) in KG-1 cells, an Acute Myeloid Leukemia (AML) human cell line, tumor cell death being measured by analysing PKH26+AnnexinV+cells, the cells being treated with no Alendronate (No drug and liposome present), drug-free (blank) Stealth liposomes (Stealth:Drug-free liposomes), Alendronate (20 μg/ml, Free Alendronate), liposomes co-encapsulating alendronate and doxorubicin (20 μg/ml, PLAD), folate targeted liposomes co-encapsulating alendronate and doxorubidin (20 μg/ml, PLAD-FT), and Doxil (13.3 μg/ml, Doxil), following by incubation with γδ T-cells, at a ratio of 1 tumor cell to 1 T-cell (▨), 1 tumor cell to 5 T-cells (▨) or with no γδ T-cells (▨). In addition, 100 U/mL of IL-2 was also given.

The γδ T-cells used in these assays were from two different AML patients. FIG. 11 show that alendronate enhances tumour sensitivity to γδ T-cells' cytotoxic action. However, doxorubicin in the form of Doxil did not result in significant enhancement. Interestingly, when both drugs, ALD and DOX are delivered in the same liposome with or without folate targeting (PLAD or FT-PLAD) together, the highest percentages of killing within the period of the 4 h of the assay was achieved In addition, it was noted that, in the L-ALD/DOX and the folate targeted version FT-L-DOX-ALD/DOX treated cells, microscopic examination revealed that many cells had undergone lysis and were not measurable by the Annexin assay, and thus, cell death was underestimated.

The invention claimed is:

1. A liposome comprising a membrane and an intraliposomal aqueous water phase, the membrane comprising at least one liposome forming lipid and the intraliposomal aqueous water phase comprising a salt of
    an N-containing bisphosphonate selected from the group consisting of alendronate, pamidronate, neridronate, olpadronate, ibandronate, risedronate and zoledronate, and
    an amphipathic weak base agent selected from the group consisting of doxorubicin, epirubicin, daunorubicin, idarubicin, amrubicin, mitoxantrone, vincristine, vinblastine, vinorelbine, topotecan, irinotecan, and 7-ethyl-10-hydroxycamptothecin (SN-38).

2. The liposome of claim 1, wherein the salt of the N-containing bisphosphonate and the amphipathic weak base agent is at least partially precipitated in the intraliposomal aqueous water phase.

3. The liposome of claim 1, comprising a cholesterol in an amount such that the phospholipid/cholesterol mole:mole ratio in the liposome's membrane is in the range of between about 75:25 and about 50:50.

4. The liposome of claim 1, wherein the liposome comprises a targeting moiety covalently linked to the liposomal outer surface.

5. A method for co-encapsulating in the same liposome an N-containing bisphosphonate and an amphipathic weak base agent having a pKa equal or below 11 and a logD at pH 7 in the range between −2.5 and 1.5, said amphipathic weak base agent being selected from the group consisting of doxorubicin, epirubicin, daunorubicin, idarubicin, amrubicin, mitoxantrone, vincristine, vinblastine, vinorelbine, topotecan, irinotecan, and 7-ethyl-10-hydroxycamptothecin (SN-38), and said N-containing bisphosphonate being selected from the group consisting of alendronate, pamidronate, neridronate, olpadronate, ibandronate, risedronate and zoledronate, the method comprising:
    (i) providing liposomes comprising a membrane and an intraliposomal water phase, the membrane comprising at least one liposome forming lipid and the intraliposomal water phase comprising encapsulated therein, the N-containing bisphosphonate; and
    (ii) incubating the liposomes encapsulating the N-containing bisphosphonate, with an amount of the amphipathic weak base agent to allow co-encapsulation of the N-containing bisphosphonate and the amphipathic weak base agent, whereby a salt between the N-containing bisphosphonate and the amphipathic weak base agent is formed.

6. The method of claim 5, wherein said N-containing bisphosphonate in the liposome prior to incubation with said amphipathic weak base agent is an ammonium bisphosphonate salt.

7. The method of claim 5, wherein the N-containing bisphosphonate is encapsulated in the liposome by rehydrating liposome forming lipids with the N-containing bisphosphonate ammonium salt in a buffer or water.

8. The method of claim 5, wherein the incubation of step (ii) is at a temperature above 40° C.

9. The method of claim 5, wherein the amount of the amphipathic weak base agent introduced into the suspension is such that the mole ratio between the amphipathic weak base agent and the N-containing bisphosphonate is between 0.1 and 2.

10. The method of claim 5, comprising removing non encapsulated N-containing bisphosphonate from the suspension of liposomes encapsulating it prior to incubation with the amphipathic weak base agent.

11. A pharmaceutical composition comprising as active ingredient liposomes as defined in claim 1, in combination with a physiologically acceptable carrier.

12. The liposome of claim 1, wherein the amphipathic weak base is an anthracycline selected from the group consisting of doxorubicin, epirubicin, daunorubicin, idarubicin and amrubicin.

* * * * *